(12) United States Patent
Choi et al.

(10) Patent No.: US 11,813,332 B2
(45) Date of Patent: Nov. 14, 2023

(54) PHOTOSENSITIZER-PEPTIDE CONJUGATE COMPRISING DEGRADABLE LINKER, AND COMPOSITION FOR PHOTODYNAMIC DIAGNOSIS OR TREATMENT COMPRISING SAME

(71) Applicant: NATIONAL CANCER CENTER, Goyang-si (KR)

(72) Inventors: Yong-Doo Choi, Goyang-si (KR); Ji-Su Kim, Incheon (KR)

(73) Assignee: NATIONAL CANCER CENTER, Goyang-si (KR)

( * ) Notice: Subject to any disclaimer, the term of this patent is extended or adjusted under 35 U.S.C. 154(b) by 221 days.

(21) Appl. No.: 16/316,555

(22) PCT Filed: Jul. 4, 2017

(86) PCT No.: PCT/KR2017/007068
§ 371 (c)(1),
(2) Date: Jan. 9, 2019

(87) PCT Pub. No.: WO2018/012778
PCT Pub. Date: Jan. 18, 2018

(65) Prior Publication Data
US 2020/0054751 A1    Feb. 20, 2020

(30) Foreign Application Priority Data
Jul. 13, 2016    (KR) .................. 10-2016-0088676

(51) Int. Cl.
*G01N 33/544*    (2006.01)
*A61K 41/00*    (2020.01)
*A61K 47/66*    (2017.01)
*A61K 38/17*    (2006.01)

(52) U.S. Cl.
CPC .......... *A61K 41/0042* (2013.01); *A61K 38/17* (2013.01); *A61K 47/66* (2017.08); *G01N 33/544* (2013.01)

(58) Field of Classification Search
None
See application file for complete search history.

(56) References Cited

U.S. PATENT DOCUMENTS

2017/0290919 A1* 10/2017 Tsubusaki et al.

FOREIGN PATENT DOCUMENTS

| KR | 10-1344303 B1 | 12/2013 |
| KR | 10-2015-0128103 A | 11/2015 |
| WO | 2009/046220 A2 | 4/2009 |
| WO | 2016/063959 A1 | 4/2016 |

OTHER PUBLICATIONS

Fontenot, Krystal R. et al., "Targeting of the epidermal growth factor receptor with mesoporphyrin IX-peptide conjugates," J. Porphyrins Phthalocyanines, vol. 20, pp. 352-366, 2016 (also cited in the Jan. 9, 2019 IDS).*
Hyunjin et al., "Photosensitizer-conjugated polymeric nanoparticles for redox-responsive fluorescence imaging and photodynamic therapy," J. Mater. Chem. B, vol. 1, pp. 429-431, 2013 (also cited in the Jan. 9, 2019 IDS).*
Fontenot et al. Targeting of the epidermal growth factor receptor with mesoporphyrin IX-peptide conjugates. Journal of Porphyrins and Phthalocyanines (2016),20(1/4), 352-366. https://pubmed.ncbi.nlm.nih.gov/27738394/.*
Fontenot, Krystal R. et al., "Targeting of the epidermal growth factor receptor with mesoporphyrin IX-peptide conjugates," J. Porphyrins Phthalocyanines, vol. 20, pp. 352-366, 2016.
Kim, Hyunjin et al., "Photosensitizer-conjugated polymeric nanoparticles for redox-responsive fluorescence imaging and photodynamic therapy," J. Mater. Chem. B, vol. 1, pp. 429-431, 2013.
Salerno, Allen et al., "Covalent Modification with Concomitant Inactivation of the cAMP-dependant Protein Kinase by Affinity Labels Containing Only L-Amino Acids," J. Biol. Chem., vol. 268, No. 18, pp. 13043-13049, Jun. 25, 1993.
Khananshvili, Daniel et al., "Positively Charged Cyclic Hexapeptides, Novel Blockers for the Cardiac Sarcolemma Na+—Ca2+ Exchanger," J. Biol. Chem., vol. 270, No. 27, pp. 16182-16188, Jul. 7, 1995.
Schmitt, Frederic et al., "Drug Targeting Strategies for Photodynamic Therapy," Anti-Cancer Agents in Medicinal Chemistry, vol. 12, No. 5, pp. 500-525, 2012.
Kim, Jisu et al., "Photosensitizer-conjugated tryptophan-containing peptide ligands as new dual-targeted theranostics for cancers," Int. J. Pharm, vol. 513, pp. 584-590, 2016.
Kim, Jisu et al., "A redox-responsive theranostic agent for target-specific fluorescence imaging and photodynamic therapy of EGFR-overexpressing triple-negative breast cancers," J. Mater. Chem. B, vol. 4, No. 42, pp. 6751-6884, Nov. 14, 2016.
Ongarora, Benson G. et al., "Phthalocyanine-Peptide Conjugates for Epidermal Growth Factor Receptor Targeting," J. Med. Chem., vol. 55, pp. 3725-3738, 2012.
Mansoor, Steven E. et al., "Distance Mapping in Proteins Using Florescence Spectroscopy: The Tryptophan-Induced Quenching (TrIQ) Method," Biochemistry, vol. 49, pp. 9722-9731, 2010.
Extended European Search Report for European Application No. 17827852.9, dated Jan. 30, 2020 (40 pages).
Charles Spangler et al., "Optimization of targeted two-photon PDT triads for the treatment of head and neck cancers" Photonic Thereapeutics and Diagnostics VIII, Proc. Of SPIE, vol. 8207, No. 1, Feb. 3, 2012, pp. 1-8 (8 pages).

(Continued)

*Primary Examiner* — Maury A Audet
(74) *Attorney, Agent, or Firm* — Sughrue Mion, PLLC

(57) ABSTRACT

The present invention relates to a conjugate for photodynamic diagnosis or treatment in which a peptide binds with a photosensitizer via an intracellularly degradable linkage, and to a composition for photodynamic diagnosis or treatment including the same.

7 Claims, 11 Drawing Sheets
Specification includes a Sequence Listing.

(56) References Cited

OTHER PUBLICATIONS

Noemie Thomas et al., "Tissue distribution and pharmacokinetics of an ATWLPPR-conjugated chlorin-type photosensitizer targeting neuropilin-1 in glioma-bearing nude mice", Photochemical & Photobiological Sciences, vol. 7, No. 4, Jan. 1, 2008, p. 433-441 (9 pages).
Japanese Office Action and English Translation for Japanese Application No. 2019-501915, dated Feb. 12, 2020 (8 pages).

* cited by examiner

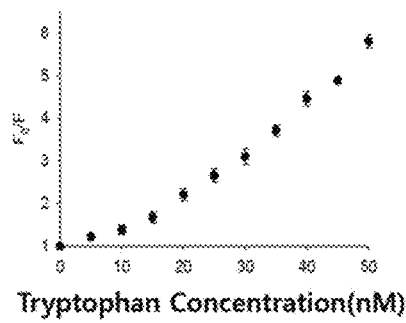
FIG. 2A
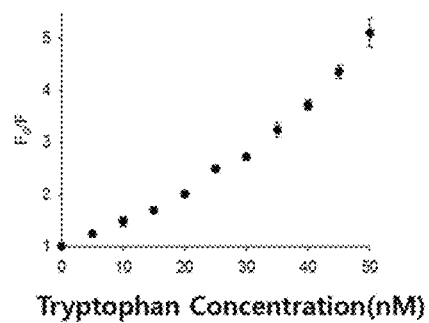
FIG. 2B
FIG. 3
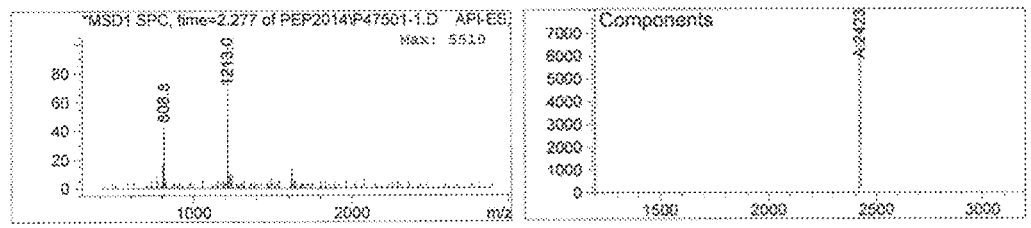

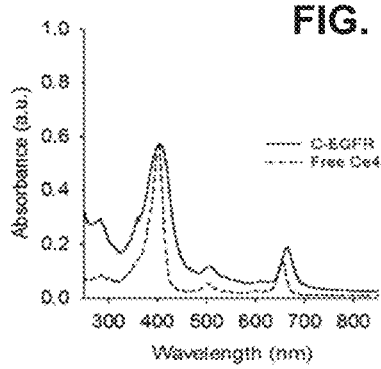
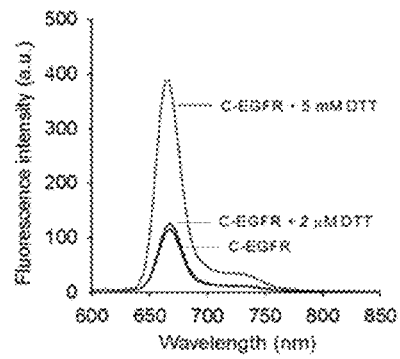
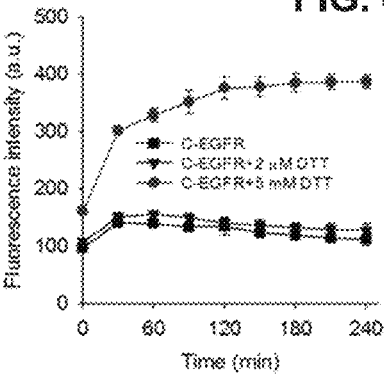
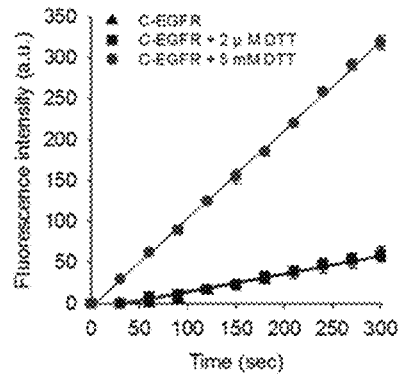
FIG. 4A
FIG. 4B
FIG. 4C
FIG. 4D
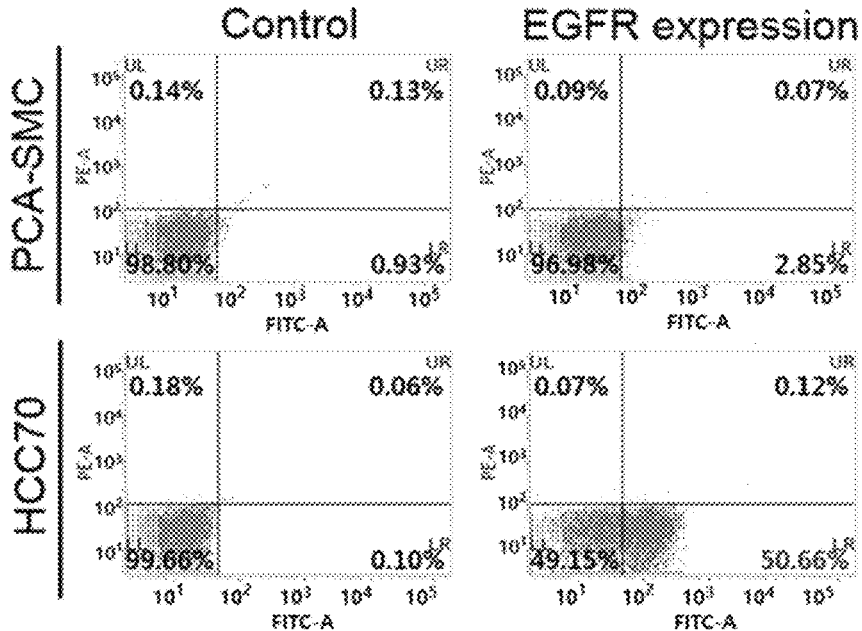
FIG. 5

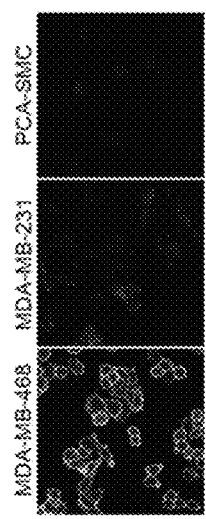 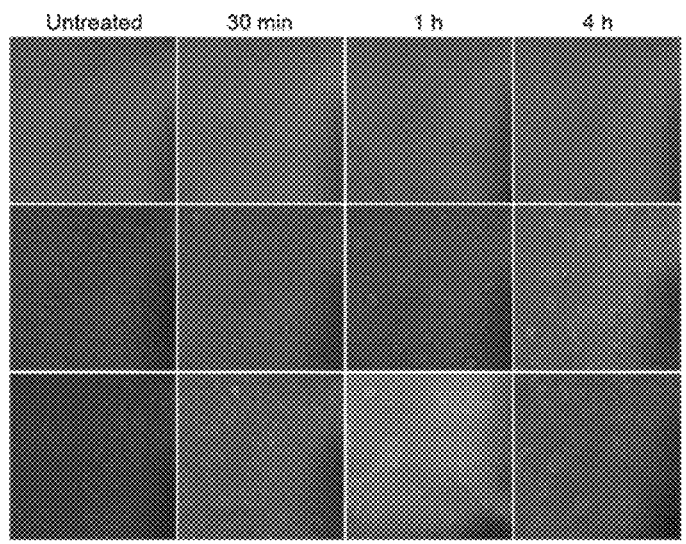
FIG. 12A  FIG. 12B
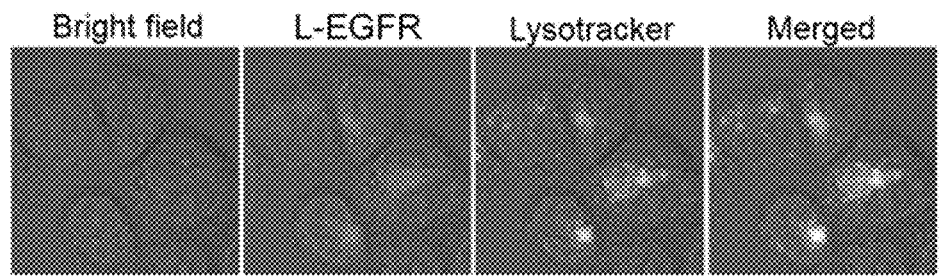
FIG. 13
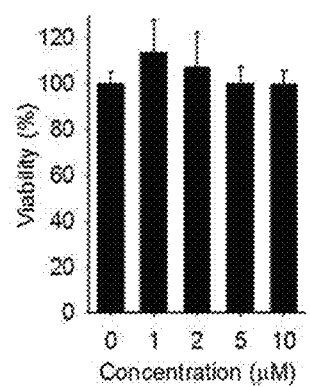 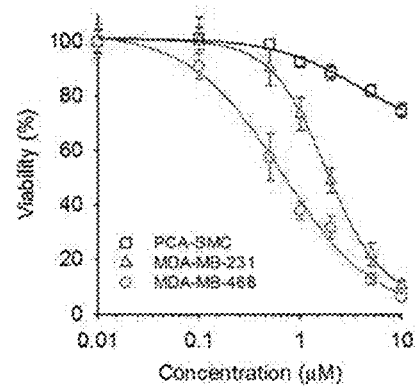
FIG. 14A  FIG. 14B

PHOTOSENSITIZER-PEPTIDE CONJUGATE COMPRISING DEGRADABLE LINKER, AND COMPOSITION FOR PHOTODYNAMIC DIAGNOSIS OR TREATMENT COMPRISING SAME

TECHNICAL FIELD

The present invention relates to a conjugate for photodynamic diagnosis or treatment in which a peptide is conjugated with a photosensitizer via an intracellularly degradable linkage, and to a composition for photodynamic diagnosis or treatment including the same.

BACKGROUND ART

Photodynamic therapy (PDT) is a technology of treating malignant diseases such as cancers or treating diseases such as acne without performing a surgical operation by using a photosensitive material (hereinafter, referred to as "photosensitizer"). Such PDT has been actively studied from the early 21st century, and currently, is being used in order to increase immunity in cancer diagnosis and therapy, autologous bone marrow transplantation, antibiotics, AIDS therapy, skin graft, or arthritis therapy, and thus the application range thereof has gradually widened.

In particular, as for PDT used in cancer therapy, when a photosensitizer, which is a material sensitive to light, is administered into the body and external light is irradiated, the photosensitizer chemically reacts with fluent oxygen in the external light, to generate singlet oxygens or free radicals, and these singlet oxygens or free radicals induce apoptosis in various lesions and cancer cells to destroy them.

Currently, porphyrin derivatives, chlorine, bacteriochlorin, phthalocyanine, 5-aminolevulinic acid derivatives, and the like have been known as the photosensitizer used in PDT. Cyclic tetrapyrrole derivatives as the photosensitizer are characterized by being selectively accumulated in cancer cells and exhibiting fluorescence or phosphorescence due to compound property, and thus may be utilized as a reagent for early diagnosis. In addition, since metalloporphyrin in which metal is bound inside the cyclic tetrapyrrole exhibits several characteristics depending on the kind of metal bound thereto, metalloporphyrin is used as a contrasting agent at the time of magnetic resonance imaging (MRI) and thus is applied during the early diagnosis of tumor cells such as cancer cells. Also, 5-aminolevulinic acid derivatives, which are the most widely known photosensitizers, are simply used and have a small molecular weight, which thus comparatively facilitate skin permeation, and have few side effects and thus are stable.

However, the photosensitizer for photodynamic diagnosis or therapy used in the related art has low accumulation rate and target specificity to cancer cells and does not induce fluorescence interference, and thus exhibits cytotoxicity in general cells, that is, normal cells in vivo when the light is irradiated, resulting in reduced therapeutic outcomes and causing several side effects. That is, conventionally, the photosensitizers used in photodynamic therapy have a hydrophobic characteristic, so that after intravenous injection, it accumulates nonspecifically in normal tissues including skin as well as cancer tissues. This not only makes the tumor-to-background ratio worse and thus makes diagnostic imaging of the tumor site difficult, but also has the risk of damaging the important normal tissues during photodynamic therapy. Moreover, when a patient receiving photodynamic therapy is exposed to bright light such as sunlight, reactive oxygen is generated again from the photosensitizer that has accumulated in the skin, resulting in side effects of skin photosensitivity. For this reason, after photodynamic therapy, the patient is recommended to remain in the dark room for at least 6 weeks until the photosensitizer accumulated in the normal tissues of the skin, etc., disappears, which causes discomfort to the patient. There is an attempt to solve the skin photosensitivity problem by increasing the hydrophilicity of the photosensitizer, but in this case, since a large amount of the intravenously administered photosensitizer is excreted through urine, in order for a sufficient amount of photosensitizer for therapy to be accumulated in the tumor tissue, a higher dose of photosensitizer should be administered.

As a means for solving these problems and enhancing tumor selectivity, by developing a peptide-photosensitizer conjugate in which a peptide capable of specifically binding to a receptor or the like over-expressed on the surface of cancer cells is linked to a photosensitizer, an attempt was made so that the photosensitizer can be specifically introduced only into the target cancer cells. However, the peptide-photosensitizer conjugates that have been developed previously still have a disadvantage in that they generate fluorescence signals when they are outside the target cells or are introduced into the cells and exhibit phototoxicity, and even in the case of nonspecific adsorption to normal cells, it is phototoxic to normal cells when exposed to light. Accordingly, there was a limit in that one had to wait until the peptides-fluorescent dyes or peptide-photosensitizer conjugates that are circulating in blood or accumulated nonspecifically in normal cells are removed via urinary excretion or metabolism, and thereafter obtain fluorescence images or perform photodynamic therapy. However, since the pharmacokinetic characteristics are different depending on patients, there is a problem that it is difficult to know the optimal time for imaging or photodynamic therapy, and there is a limit to obtaining the tumor selective photodynamic therapy effect.

DISCLOSURE

Technical Problem

Accordingly, the present invention is designed to solve the problems that conventional fluorescent dyes and photosensitizers generally rely on cell permeability, resulting in low accumulation rate and target rate of cancer cells, low tumor-to-background signal ratio due to autofluorescence, significantly different in residence time affected by different pharmacokinetic characteristics among subjects, and generating noise in the fluorescence activated image. To this end, an attempt has been made to develop a photosensitizer-peptide conjugate with linker that does not produce fluorescence signals in its native state but selectively produces a strong fluorescence signal only when it enters the target cell (for example, cancer cells), so as to enable image detection of target cells with high tumor-to-background signal ratio without time limitation.

In addition, in the case of the degradable photosensitizer-peptide conjugate of the present invention, reactive oxygen is not produced when it is present outside the target cell, and reactive oxygen generation is activated only when it is ingested and entered into the target cell. By providing a target cell-specific photodynamic therapy effect, the present invention aims at inhibiting non-specific damage to normal tissues.

Technical Solution

In order to accomplish the above object, the present invention provides a conjugate, including: a photosensitizer; a peptide including tryptophan, and a linker for linking the photosensitizer and the peptide by a covalent bond.

According to one embodiment of the present invention, the distance between the photosensitizer and the tryptophan of the peptide may be within 2 nm. When the tryptophan is located close within 2 nm of the photosensitizer, a photoinduced electron transfer phenomenon occurs between the tryptophan and the photosensitizer. In this case, the photosensitizer is quenched, and may be induced not to generate a fluorescence signal and not to produce reactive oxygen.

According to one embodiment of the present invention, the linker used for making the distance between the tryptophan and the photosensitizer to be within 2 nm is a linker capable of degradation in the cells, which is degraded by an intracellular reducing agent or an intracellular enzyme, or may be any one or more selected from a linkage which is degraded in an intracellular pH 4 to 5.5 environment.

According to one embodiment of the present invention, a conjugate of a degradable linker; a peptide including tryptophan, and a photosensitizer may be further conjugated to antibodies, aptamers, and peptide ligands capable of targeting specific cells, which further enhances the specific uptake capacity of the targeted cells.

According to one embodiment of the present invention, when tryptophan is already included in a peptide ligand capable of specifically binding to the surface of a specific cell, a peptide ligand and a photosensitizer may be linked to a degradable linker.

According to one embodiment of the present invention, the peptide including tryptophan may specifically bind to one or more epidermal growth factor receptors selected from the group consisting of epidermal growth factor receptor 1, epidermal growth factor receptor 2, epidermal growth factor receptor 3, and epidermal growth factor receptor 4.

According to one embodiment of the present invention, the peptide including tryptophan may have the amino acid sequence represented by SEQ ID NO: 1, and the tryptophan may be present in the peptide in a sequence of one to three or less.

According to one embodiment of the present invention, the linker may be a conjugate of a linear disulfide bond or a cyclic disulfide bond.

According to one embodiment of the present invention, the linker may be a peptide, such as arginine, lysine or a combination thereof, and the peptide may be composed of 3 or less amino acid sequences, and the linker may include a disulfide bond and a di-arginine; or a disulfide bond and a di-lysine, which may be located between the photosensitizer and the peptide in a cyclic form, and the cyclic form may be formed by binding cysteine to both ends of the di-arginine or di-lysine.

According to one embodiment of the present invention, it may be a conjugate represented by Formulas 1 to 7.

[Formula 1]

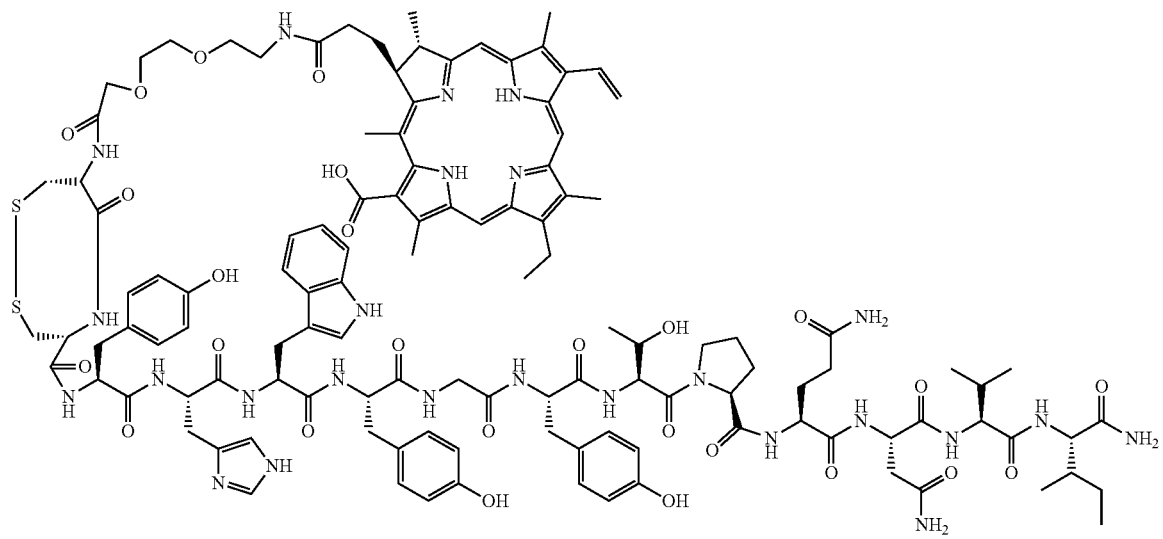

[Formula 2]
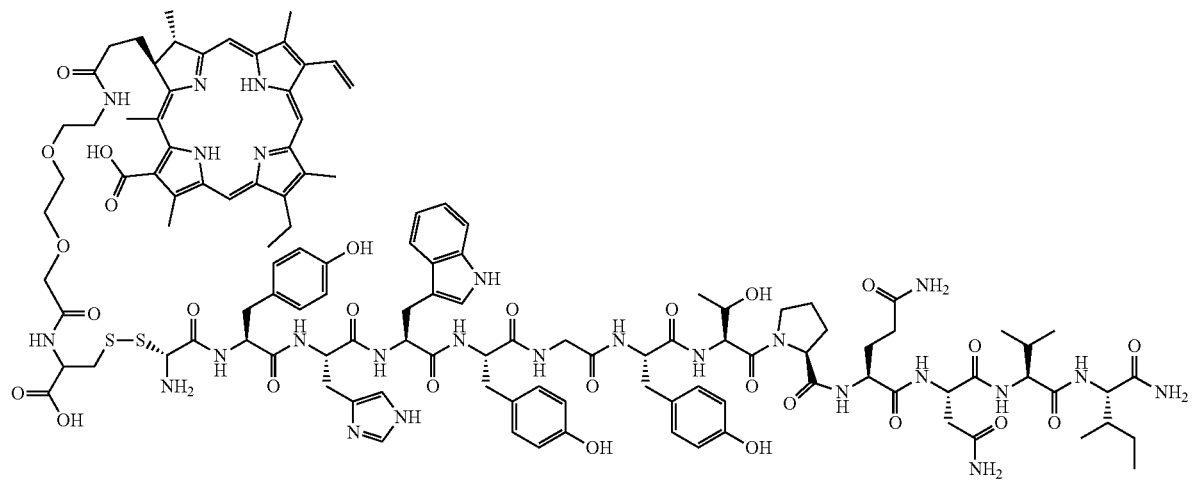
[Formula 3]
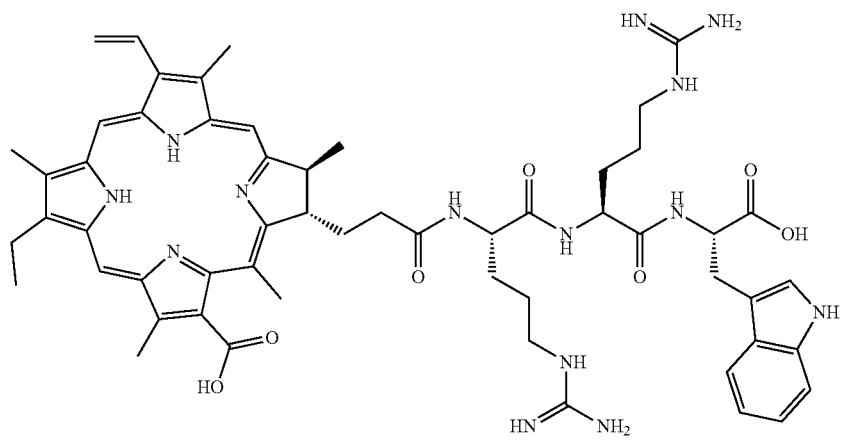
[Formula 4]
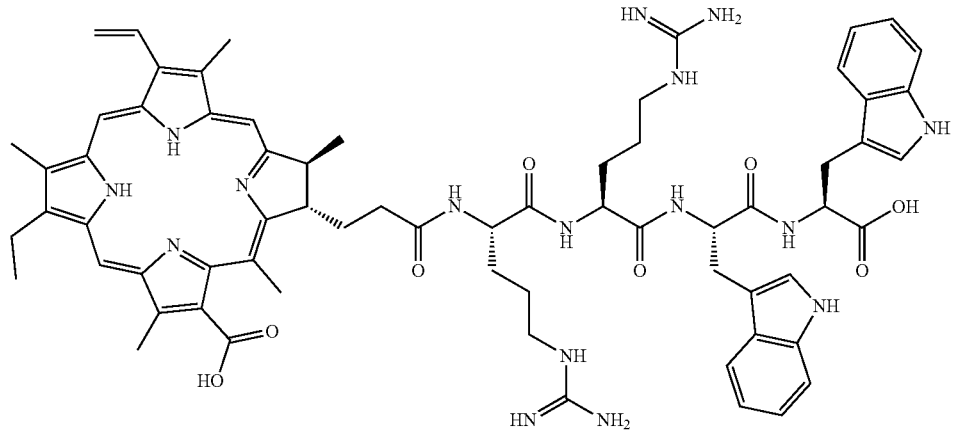

-continued

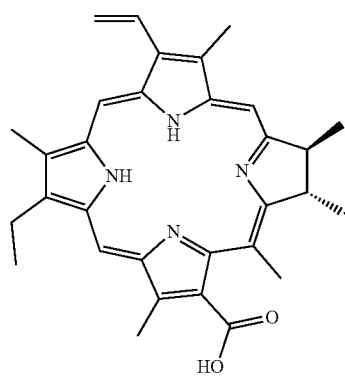
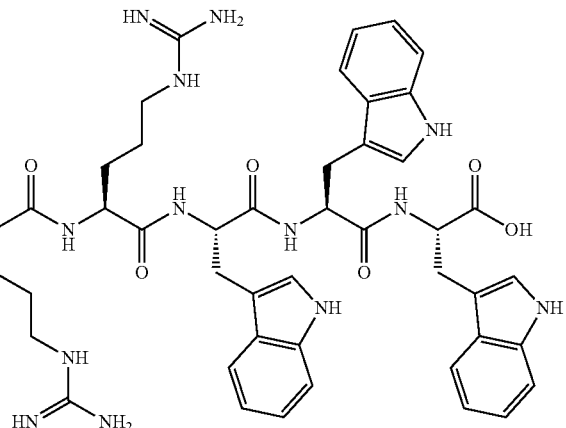

[Formula 5]

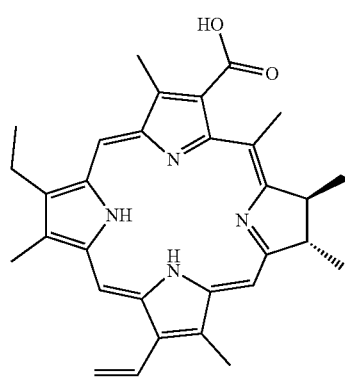
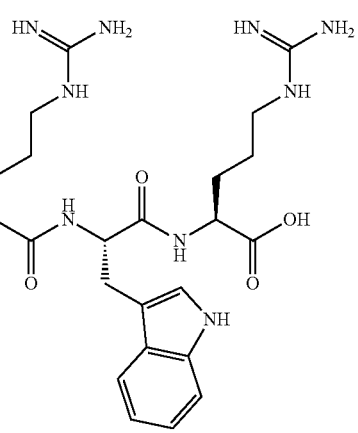

[Formula 6]

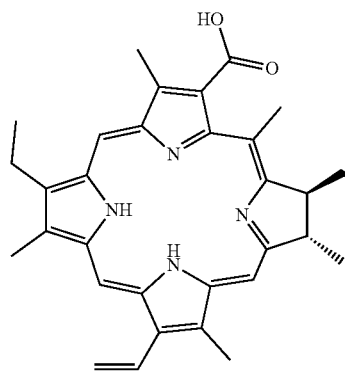
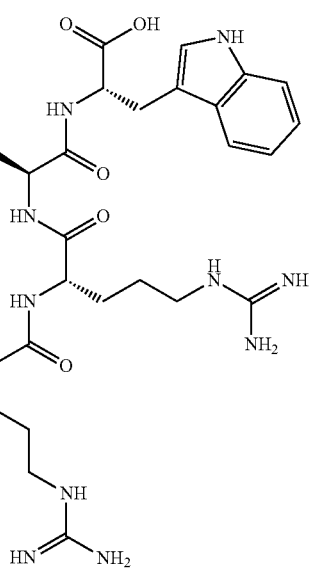

[Formula 7]

Advantageous Effects

In the photosensitizer-peptide conjugate of the present invention, when the distance between the photosensitizer and the tryptophan is maintained within 2 nm through the degradable linkage, the conjugate generates no fluorescent signal and reactive oxygen species in normal tissues or during the circulation in the blood by quenching a fluorescent signal and reactive oxygen generation ability of the photosensitizer. After the conjugate of the present invention is selectively absorbed into cells by interaction with an overexpressed antigen on the surface of the target cells, a linker is degraded in the cells to increase the distance between tryptophan included in the peptide and the photosensitizer, which becomes farther than 2 nm, and the quenching action is terminated to generate a strong fluorescence signal and induce active generation of reactive oxygen species. Therefore, the conjugate for photodynamic diagnosis or treatment including a peptide according to the present invention has high tissue permeability, shows a high photodynamic therapeutic effect only in target cells (for example, cancer cells) while being safe in normal cells, and can obtain a good diagnostic image having a high ratio of target-to-background signal ratio.

DESCRIPTION OF DRAWINGS

FIGS. 2A-2B illustrate the results of experiments illustrating the quenching effect of tryptophan on the photosensitizer of the present invention (FIG. 2A obtains the ratio of the fluorescence signal (F) when tryptophan is added as compared to the fluorescence signal ($F_0$) when no tryptophan is added ($\lambda_{Ex.}$ 400 nm, $\lambda_{Em.}$ 665 nm) while fixing the concentration of chlorin e4 (Ce4) at a concentration of 5 µM and increasing the concentration of tryptophan; FIG. 2B obtains the ratio of the fluorescence signal (F) when tryptophan is added as compared to the fluorescence signal ($F_0$) when no tryptophan is added (concentration 5 µM, $\lambda_{Ex.}$ 660 nm, $\lambda_{Em.}$ 690 nm) while fixing the concentration of Al(III) phthalocyanine chloride tetrasulfonic acid(AlPcS4) at a concentration of 5 µM and increasing the concentration of tryptophan).

FIG. 3 is mass spectrometry data of a C-EGFR which is a photosensitizer-peptide conjugate including a cyclic disulfide bond linker synthesized in Example 2 of the present invention.

FIG. 4A compares the UV/Vis absorption spectrum of a C-EGFR which is a photosensitizer-peptide conjugate including a cyclic disulfide bond linker synthesized in Example 2 of the present invention, and a free dye.

FIG. 4B observes the changes in fluorescence spectra, respectively, of the case when the C-EGFR of Example 2 of the present invention is treated with PBS aqueous solution, when it is treated with a reducing agent dithiothreitol (DTT) at a concentration of 2 µM for 4 hours, and when it is treated at a concentration of DTT 5 mM for 4 hours ($\lambda_{Ex.}$ 400 nm).

FIG. 4C observes the changes in fluorescence spectra with time ($\lambda_{Ex.}$ 400 nm, $\lambda_{Em.}$ 665 nm), respectively, of the C-EGFR of Example 2 treated with PBS solution, a reducing agent dithiothreitol (DTT) at a concentration of 2 µM and 5 mM.

FIG. 4D is a graph that analyses the generation of singlet oxygen by irradiating 670 nm laser with the C-EGFR of Example 2 treated with PBS solution, DTT 2 µM and 5 mM, respectively.

FIG. 5 illustrates the results of analysis of the epithelial growth factor receptor (EGFR) expression level in human normal cell line (PCA-SMC) and human breast cancer cell line (HCC70) used in Example 2 using a flow cytometer (it was confirmed that PCA-SMC cells are EGFR negative cell lines and HCC70 cells are EGFR positive cell lines).

FIG. 12A is data that analyzes the expression of epidermal growth factor receptor (EGFR) in human normal cell line PCA-SMC, human breast cancer cell lines MDA-MB-231 and MDA-MB-468 through immunocytochemical staining (Nuclei are stained blue and an EGFR on cell surface is stained green).

FIG. 12B is a confocal laser microscope photograph obtained by treating the L-EGFR conjugate of Example 3 with PCA-SMC, MDA-MB-231 and MDA-MB-468 cell lines in each time period, respectively ($\lambda_{Ex.}$ 404 nm, $\lambda_{Em.}$ 625~754 nm).

FIG. 13 is a confocal laser microscope photograph of the L-EGFR conjugate of Example 3 treated with MDA-MB-468 cells together with LysoTracker.

FIG. 14A is data of the cell survival rate of MDA-MB-468, a human breast cancer cell line, treated with various concentrations of RedoxT in order to analyze the cytotoxicity of the L-EGFR conjugate of Example 3.

FIG. 14B is data that analyses the cell survival rate obtained by treating PCA-SMC cells and MDA-MB-231 and MDA-MB-468 cells with various concentrations of RedoxT for 4 hours and washing the same in order to verify the effect of the target cell-specific photodynamic therapy on the L-EGFR conjugate of Example 3, followed by irradiation of 670 nm laser to perform photodynamic therapy.

BEST MODES OF THE INVENTION

Figure 1A:
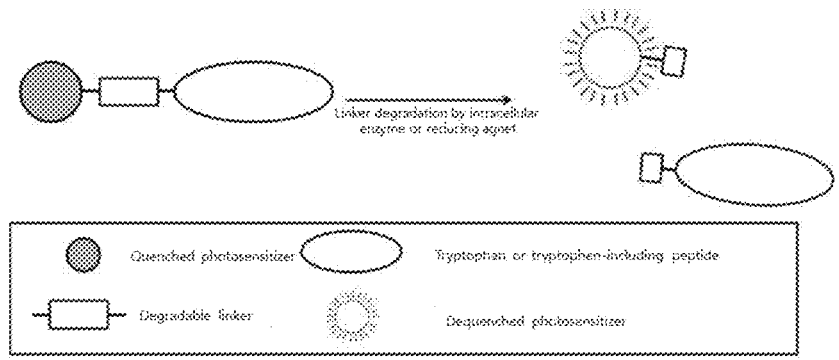
FIG. 1A is a schematic diagram illustrating the structure and characteristics of a photosensitizer-peptide conjugate including a degradable linker.

In order to achieve the above object, the present invention provides a conjugate for photodynamic diagnosis or treatment in which a tryptophan or a peptide including the tryptophan is conjugated with a photosensitizer via an intracellularly degradable linkage, and a composition for photodynamic diagnosis or treatment including the same.

Unless otherwise defined, the term "treatment" indicates the action that can reverse or relieve the disease itself or one or more symptoms of the disease targeted by the term, or that can inhibit the progress or prevent the target disease. As used herein, the term "treatment" refers to an act of treating when "treatment" is defined as above.

The main function of the tryptophan in the present invention is to prevent the fluorescence signal from being generated from the conjugate by acting as a quenching agent when the distance on the three-dimension with the bound photosensitizer is within 2 nm, and to inhibit the generation of therapeutic reactive oxygen species. After the conjugate is entered into target cells, a linker in the conjugate is degraded inside the cells to increase the distance between tryptophan and the photosensitizer to 2 nm or more, and the quenching action by tryptophan is terminated. From this time on, strong fluorescence signals are generated to enable fluorescence imaging diagnosis specific to target cells, and active generation of reactive oxygen species is also induced, thereby enabling selective photodynamic therapy. In particular, when the tryptophan and the photosensitizer conjugate bound via a degradable linker is further bound to an antibody, RNA or DNA aptamer, a peptide ligand, a nanoparticle, or the like capable of binding to a specific cell, it further improves the specificity to target cells.

When the peptide itself capable of specific binding to a specific cell includes tryptophan, the distance between the tryptophan and the photosensitizer may be induced to be within 2 nm by conjugating the peptide and the photosensitizer via a degradable linker. Also at this time, a quenching phenomenon of the photosensitizer may be obtained. The thus-quenched fluorophore (or photosensitizer) and the peptide conjugate is absorbed only into target cells of the peptide-photosensitizer conjugate by specifically bound to the surface of target cancer cells and inflammatory cells, and be entered into the target cells, the linker is degraded and the distance between the tryptophan and the fluorophore (or photosensitizer) is increased to 2 nm or more, and the quenching action by tryptophan is terminated. From this time on, strong fluorescence signals are generated to enable fluorescence imaging diagnosis specific to target cells, and active generation of reactive oxygen species is also induced, thereby enabling selective photodynamic therapy.

The intracellularly degradable linkage means that it can be degraded by an intracellular environment such as an enzyme, a signaling factor, a reducing agent, and a pH, and more specifically, it may be degraded in lysosome. Therefore, the intracellular degradable linkage may be any one or more selected from linkages that are degraded by intracellular enzymes, linkages that are degraded by intracellular reducing agents, or linkages that are degraded by intracellular low pH.

The enzyme that degrades a linker included in a conjugate for photodynamic diagnosis or treatment of the present invention may be any one selected from cathepsins and esterases or a combination thereof, and the cathepsins may be any one or more enzymes selected from the group consisting of cathepsin B, cathepsin L and cathepsin S. For example, it may be a bond consisting of arginine or lysine which is degraded by cathepsin B present in lysosome, an ester (—COO—) or a thioester (—COS—) bond which is degraded by esterase.

The intracellular reducing agent capable of degrading a linker included in a conjugate for photodynamic diagnosis or treatment of the present invention may be at least one selected from the group consisting of glutathione, sulfhydryl and nicotinamide adenine dinucleotide phosphate (NADPH), and may be, for example, a disulfide bond that may be degraded by glutathione in the lysosome. Glutathione is known to be present at a concentration of about 2 μM in the extracellular region including blood and at a high concentration of 10 mM in cancer cells.

A schematic diagram of the action of the present invention is illustrated in FIG. 1. FIG. 1A is a schematic diagram schematically illustrating the structure and characteristics of a photosensitizer-peptide conjugate including a degradable linker. Peptides including photosensitizers and tryptophan or photosensitizers and tryptophan are bound via an intracellularly degradable linker, and the distance between tryptophan and photosensitizer to maximize the quenching effect of a photosensitizer by tryptophan is within 2 nm.

Figure 1B:
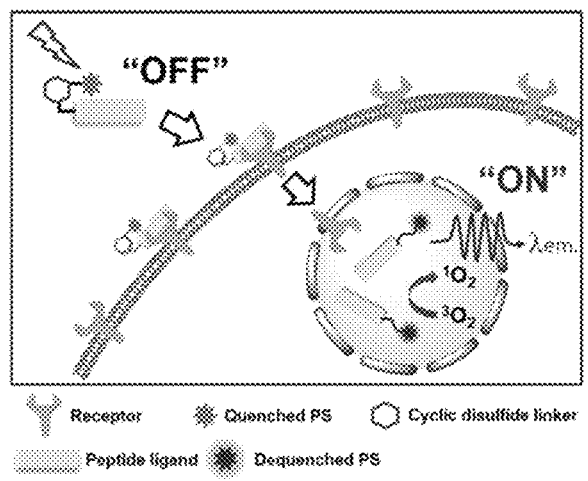
FIG. 1B is a schematic diagram illustrating the efficacy of a photosensitizer-peptide conjugate including a degradable cyclic linker.
Figure 1C:
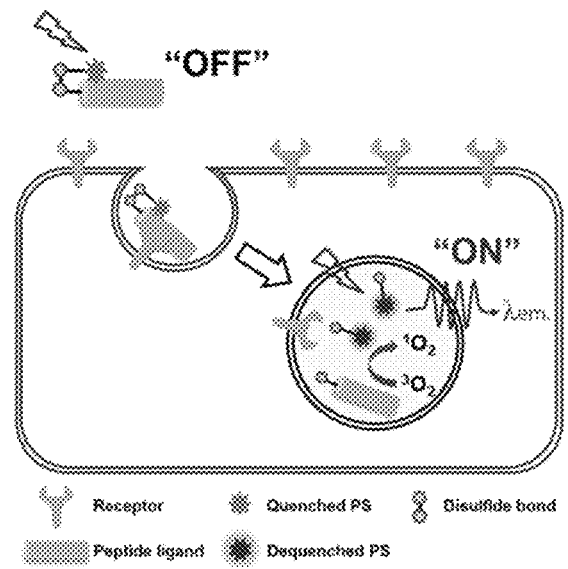
FIG. 1C is a schematic diagram illustrating the efficacy of a photosensitizer-peptide conjugate including a degradable linear linker.

More preferably, the distance on the three-dimension may be within 2 nm. When the intracellular degradable linker is cleaved in target cells and the distance between the tryptophan and the photosensitizer is further increased to 2 nm or more, the quenching effect by tryptophan is terminated and strong fluorescence signals are generated from the photosensitizer, thereby producing a photodynamic treatment effect (FIG. 1B and FIG. 1C). The linker may be degraded by an intracellular enzyme or a reducing agent by a single or a combination action.

As the photosensitizer used for photodynamic diagnosis or therapeutic conjugation according to the present invention, a photosensitizer that may be applied by a person skilled in the pertinent field may be applied. For example, it may be used from the group consisting of the porphyrin-based compound selected from the group consisting of porphyrins, chlorins, pheophorbides, bacteriochlorins, porphycenes, and phthalocyanines, or the non-porphyrin-based compound selected from the group consisting of hypericin, rhodamine, rose bengal, psoralen, phenothiazinum-based dyes and merocyanine, but is not limited thereto. More specifically, it may use those, alone or in combination, selected from the group consisting of the porphyrin-based compound selected from the group consisting of hematoporphyrins, porphycenes, pheophorbides, purpurins, chlorins, protoporphyrins, phthalocyanines in the form of free bases or metal complexes; or the non-porphyrin-based compound selected from the group consisting of hypericin, rhodamine, ATTO, rose Bengal, psoralen, phenothiazinium-based dyes and merocyanine.

In the present invention, when the conjugate of the present invention is selectively accumulated in cancer tissue, fluorescent interference is released by the action of a reducing agent or an enzyme in cancer cells, and since the photosensitizer can exhibit fluorescence only in cancer cells by laser irradiation, this fluorescence can diagnose cancer. In addition, reactive oxygen generation that has been suppressed is activated again, so that a target cell-specific photodynamic therapy effect can be obtained.

The present invention provides a composition for photodynamic diagnosis or treatment including the conjugate for photodynamic diagnosis or treatment.

The composition for photodynamic therapy according to the present invention may include a pharmaceutically effective amount of the conjugate for photodynamic diagnosis or therapy of the present invention alone, or may further include at least one pharmaceutically acceptable carrier, excipient, or diluent. The term pharmaceutically effective amount means an amount sufficient to prevent, improve, and treat symptoms of diseases.

The pharmaceutically effective amount of the conjugate for photodynamic diagnosis or therapy according to the present invention is 0.5~100 mg/day/kg body mass, and preferably 0.5~5 mg/day/kg body mass. However, the pharmaceutically effective amount may be appropriately varied depending on the severity of the symptom, age, weight, health status, and gender of the patient, route of administration, duration of treatment, and the like.

Herein, the term pharmaceutically acceptable carrier, excipient or diluent means a composition that is physiologically acceptable and does not generally cause gastrointestinal disorders, allergic reactions such as dizziness, or similar reactions when being administered to a human. Examples of the carrier, excipient, and diluent may be lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate, and mineral oil. In addition, they may further include filler, anti-coagulant, lubricant, wetting agent, flavoring, emulsifier, and preservative.

In addition, the composition of the present invention may be formulated by using the method known in the art so that an active component is provided in a manner of fast release, sustained release, or delayed release after the composition is administered to a mammal. The dosage form may be powder, granule, tablet, emulsion, syrup, aerosol, soft or hard gelatin capsule, sterile injectable solution, or sterile powder.

The composition for photodynamic therapy according to the present invention may be administered through several routes including oral, transdermal, subcutaneous, intravenous, and muscular routes, and the dosage of the active component may be appropriately selected depending on several factors such as route of administration, age, gender, weight, and severity of symptom of the patient.

In addition, in the case where the conjugate according to the present invention or the composition including the conjugate is used to conduct therapy or diagnosis of diseases, a light source usable in the present invention may be, but is not limited thereto, at least one selected from the group consisting of light sources for in vitro light irradiation selected from the group consisting of an ultrasonic irradiation emitter, a light emitting diode, a laser diode, a dye laser, a halogenated metal lamp, a flash lamp, a mechanically filtered fluorescent light source, a mechanically filtered incandescence, a filament light source, and the like; and light sources for in vivo light irradiation including a laser fiber for photodynamic therapy and the like. In the present invention, the photosensitizer may exhibit activity in the near infrared ray in the range of 600 nm to 900 nm.

MODES OF THE INVENTION

Hereinafter, the present invention will be described in more detail with reference to examples. It is to be understood, however, that these examples are for illustrative purposes only and are not to be construed as limiting the scope of the present invention.

[Example 1] Analysis of Quenching Effect of a Photosensitizer by Tryptophan

Experiments were conducted to confirm the quenching effect of tryptophan on the photosensitizer.

More specifically, in order to confirm that the quenching effect occurs as the distance between the photosensitizer and the tryptophan approaches, Chlorin e4 (Ce4) and AlPcS4A1 (III) (phthalocyanine chloride tetrasulfonic acid), which are representative chlorine and cyanine photosensitizers, were used for the analysis. The concentration of Ce4 and A1PcS4 was fixed at a concentration of 5 μM and the ratio of the fluorescence signal (F) when tryptophan was added to the fluorescence signal ($F_0$) when tryptophan was not added while increasing the concentration of tryptophan was obtained. (Ce4: $\lambda_{Ex.}$ 400 nm, $\lambda_{Em.}$ 665 nm; A1PcS4: $\lambda_{Ex}$ 660 nm, $\lambda_{Em.}$ 690 nm). The results are illustrated in FIG. 2.

According to FIG. 2A and FIG. 2B, it can be understood that fluorescence of the photosensitizer is significantly suppressed as the concentration of tryptophan increases. When the distance between the photosensitizer and the tryptophan is sufficiently close, the photosensitizer is quenched by tryptophan.

[Example 2] Preparation and Characteristic Analysis of a Photosensitizer-Peptide Conjugate (C-EGFR) Including a Cyclic Disulfide Bond Linker In Example 2, an experiment was conducted to analyze whether the quenching effect of the photosensitizer can be controlled by controlling the distance between the tryptophan included in the peptide ligand and the photosensitizer.

As an example of peptide ligands including tryptophan, GE11 peptide (YHWYGYTPQNVI; SEQ ID NO: 1), which is known to bind specifically to the epidermal growth factor receptor (EGFR) overexpressed on the surface of cancer cells was selected, and chlorin e4 (Ce4) was used as a photosensitizer. As a degradable linker, it was selected that a disulfide bond capable of being degraded by a reducing agent present in a high concentration in a cell was inserted in a cyclic form.

2.1. Synthesis of Photosensitizer-Peptide Conjugate (C-EGFR) Including a Cyclic Disulfide Bond Linker For the synthesis of C-EGFR, peptides were prepared by Fmoc solid phase peptide synthesis (SPPS) using ASP48S (Peptron Inc, USA). The preparation process is provided as follows.

Eight equivalents of the amino acid with the protecting group (Fmoc) bound to H-Ile-2-chloro-Trityl resin (Anaspec, USA) and eight equivalents of 2-(1H-Benzotriazol-1-yl)-1,1,3,3-tetramethyluronium hexafluorophosphate (HBTU)/eight equivalents of N-Hydroxybenzotriazole (HOBt)/16 equivalents of 4-Methylmorpholine (NMM) were dissolved in Dimethylformaminde (DMF) and added, and reacted at room temperature for 2 hours, followed by washing with DMF, methanol and DMF in that orderly manner.

In order to isolate the protecting group Fmoc attached to the amino acid, DMF including 20% piperidine was added to the reaction solution and reacted twice at room temperature for 5 minutes, followed by washing with DMF, methanol and DMF in that orderly manner. This process was repeated to synthesize a resin-bound structure on the peptide scaffold [H-miniPEG2-Cys(Trt)-Cys(Trt)-Tyr(t-Bu)-His(Trt)-Trp(Boc)-Tyr(t-Bu)-Gly-Tyr(t-Bu)-Thr(t-Bu)-Pro-Gln(Trt)-Asn(Trt)-Val-Ile-2-chloro-Trityl Resin].

To the resin-peptide scaffold conjugate, four equivalents of Ce4 and four equivalents of HBTU/four equivalents of HOBt/eight equivalents of NMM were dissolved in dimethylsulfoxide (DMSO) and added, and then the mixture was reacted for 12 hours, suctioned, and then washed with DMF, methanol and DMF in that orderly manner.

When the peptide scaffold to be synthesized is formed through this process, trifluoroacetic acid (TFA)/1,2-ethanedithiol (EDT)/thioanisole/triisopropylsilane (TIS)/water were treated with solution diluted to 90/2.5/2.5/2.5/2.5 to remove the protecting group of the peptide residue prepared above and the peptide was separated from the resin to prepare [Ce4-miniPEG2-Cys(Trt)-Cys(Trt)-Tyr(t-Bu)-His(Trt)-Trp(Boc)-Tyr(t-Bu)-Gly-Tyr(t-Bu)-Pro-Gln(Trt)-Asn(Trt)-Val-Ile].

Thereafter, 10 times of cold diethyl ether was added to the reaction solution to precipitate the peptide, and centrifugation was carried out at 3000 rpm for 10 minutes. The filtrate was discarded and repeated 2 times. The conjugate thus obtained was purified by reversed phase high performance liquid chromatography (HPLC).

Peptides purified for cyclic disulfide bonds in the peptide were dissolved in 0.1% ammonium acetate solution and stirred strongly for 24 hours. The progress of the reaction was confirmed by HPLC and LC/MS. After confirming that the reaction was completed, the reaction mixture was purified by reversed phase HPLC using a Vydac C4, 5u, 300 A column (4.6×50 mm). Elution was performed using a water-acetonitrile linear gradient using 30 to 60% (v/v) acetonitrile solution including TFA 0.1%.

The chemical structure of the C-EGFR conjugate thus prepared is shown in the following Formula 1. That is, the photosensitizer and the EGFR target peptide, GE11, were bound via a cyclic disulfide bond. Due to the cyclic structure, Ce4, which is a photosensitizer, was located close to the tryptophan, and moreover, due to the limitation of mobility via a cyclic bond, Ce4 was induced to remain in close proximity to the tryptophan.

[Formula 1]

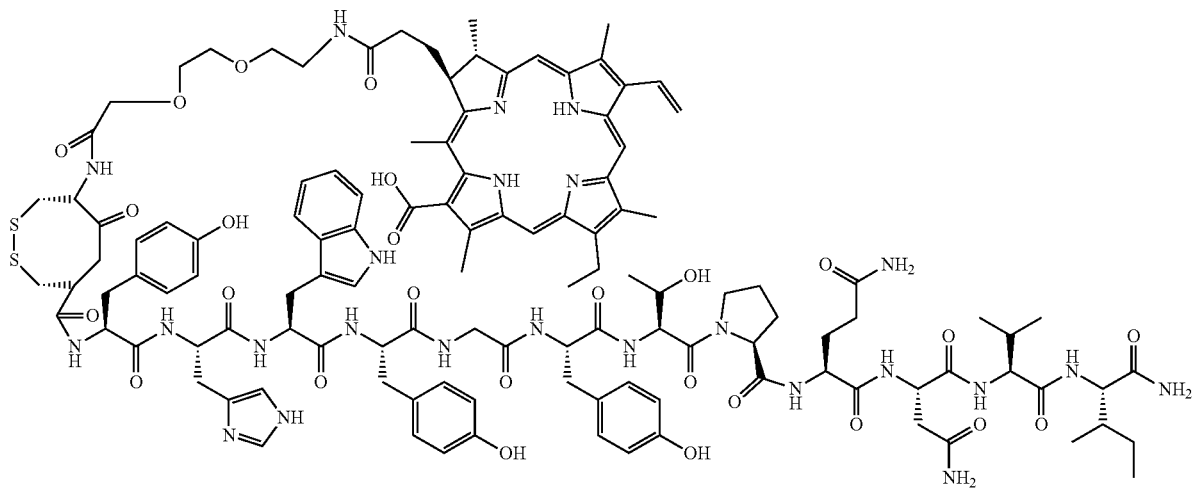

2.2. Characteristics of Cyclic C-EGFR Conjugate

1) Molecular Weight Measurement and Fluorescence Emission Characteristic Analysis The molecular weight of the synthesized and purified C-EGFR was measured using LC/MS (Agilent Hewlett Packard 1100 series, USA) and the absorbance was measured using a UV/Vis absorption spectrometer (DU370, USA).

As a result of the evaluation, the purified conjugate of the present invention thus obtained, i.e., the C-EGFR conjugate, had a molecular weight of 2,423 g/mol (FIG. 3), and the highest absorption peak was shown at 282, 402 and 665 nm (FIG. 4A). The highest emission peak was shown at 661 nm when excited at 402 nm (see FIG. 4B).

2) Analysis of Fluorescence Signal and Reactive Oxygen Generation Recovery by Reducing Agent Treatment The increase of fluorescence and reactive oxygen generation by reducing agent treatment was analyzed. The C-EGFR conjugate thus obtained was dissolved in phosphate-buffered saline (PBS, 6.7 mM, pH 7.4, 154 mM NaCl) to be 2 μM, and then transferred to a multifunctional microplate reader (Safire 2, Tecan, Switzerland) to obtain fluorescence spectrum ($\lambda_{Ex.}$ 400 nm, $\lambda_{Em.}$ 650~850 nm) results.

In the dithiothreitol (DTT) treatment sample, which is a reducing agent, 2 μM of a conjugate was mixed with 2 μM and 5 mM DTT, and the same amount of phosphate-buffered saline (PBS) was added to the buffer-treated group. The fluorescent intensity of the mixed solution (200 μl) was measured at intervals of 30 minutes for 4 hours ($\lambda_{Ex.}$ 400 nm, $\lambda_{Em.}$ 665 nm).

Singlet oxygen generation (SOG) was measured by the following method. The C-EGFR conjugate thus obtained was dissolved in PBS to be 2 μM, and then DTT-treated samples were mixed with 2 μM and 5 mM DTT, respectively, and the same amount of PBS was mixed in the buffer-treated group. The mixed solution (200 μl) was cultured at 37° C. for 4 hours. Subsequently, oxygen-saturated PBS including concentrated singlet oxygen sensor green (SOSG) was mixed and the final SOSG concentration was adjusted to 5 μM. Fluorescence intensity change of the SOSG was periodically measured using a 670 nm continuous wavelength laser device during the light irradiation (light irradiation dose: 50 mW/cm$^2$) of the sample.

According to FIG. 4, it was confirmed that fluorescence was not generated when only the C-EGFR conjugate was present (OFF state), and the fluorescence intrinsic to the photosensitizer was exhibited when disulfide bonds were degraded during 5 mM DTT treatment (ON state) (FIG. 4B). Fluorescence intensity was greatly increased by as much as 3.4 times by DTT treatment at a concentration of 5 mM. In particular, fluorescence recovered rapidly within 30 minutes after the start of the reaction and remained stable after 2 hours (FIG. 4C). In addition, when DTT was not treated or treated with 2 μM DTT at a concentration of extracellular reducing agents, the generation of singlet oxygen was inhibited. When 5 mM DTT was treated, the disulfide bond was degraded, the quenching was resolved, and singlet oxygen generation increased 5 times (FIG. 4D). Therefore, it can be understood that when the C-EGFR conjugate of the present invention is absorbed into target cells, the cyclic disulfide bond is broken and the generation of fluorescence and singlet oxygen is activated.

3) Cell Culture

The human breast cancer cell line HCC70 overexpressing epithelial growth factor receptor (EGFR) and the human normal cell line PCA-SMC (primary coronary artery smooth muscle cells) not expressing EGFR were all obtained from the American Type Culture Collection (ATCC, USA).

The HCC70 cells were cultured in RPMI (Roswell Park Memorial Institute) 1640 medium including 10% fetal bovine serum and 1% penicillin/streptomycin (Life Technologies) at 37° C. under 5% carbon dioxide and standard humidity conditions. PCA-SMC cells were cultured in a vascular cell basal medium including recombinant human insulin, ascorbic acid, glutamine, recombinant human epithelial growth factor, and fetal bovine serum 10% at 37° C. under 5% carbon dioxide and standard humidity conditions.

4) Measurement of EGFR Expression Level Using Flow Cytometer

Expression level of EGFR, a target protein, in each cell was measured by flow cytometer. PCA-SMC and HCC70 cells at 3×10$^5$ each were immobilized in a phosphate-buffered solution including 4% paraformaldehyde and washed three times.

The immobilized cells were reacted with EGFR antibody (4 μg/1 mL in 1% BSA/0.25% Tween20/PBS) for 30 minutes and washed with cold phosphate-buffered solution. Thereafter, the cells were reacted with a secondary antibody (1:100 dilution) bound with a fluorescent dye, FITC, for 30 minutes, washed once again with cold phosphate-buffered solution, and analyzed with a flow cytometer to verify the degree of EGFR expressed on the cell surface (FIG. 5).

5) Real-Time Observation of Fluorescence Quenching and Fluorescence Recovery

An experiment was conducted to verify whether a C-EGFR conjugate of the present invention in which fluorescence signal generation has been quenched from outside the target cell strongly generates fluorescence after the absorption of the C-EGFR conjugate into target cells. EGFR-overexpressing HCC70 cells were treated with the C-EGFR conjugate and free photosensitizer (Ce4), and then fluorescence images were obtained at regular time intervals without washing. The detailed method is provided as follows.

Each $1 \times 10^6$ of HCC70 cells per well were put in a 12-well plate (BD Biosciences, USA), and the cells were cultured for 24 hours to allow the cells to be absorbed well, and then C-EGFR conjugates and free photosensitizer were mixed and diluted. The existing medium was then replaced with 0.5 ml of fresh medium including the conjugate and the free photosensitizer. Thereafter, each of the near infrared light fluorescence images ($\lambda_{Ex.}$ 640±15 nm, $\lambda_{Em.}$ 690±25 nm) were obtained at intervals of 15 minutes for 4 hours using the Live Cell Imaging System (Axio Observer Z1, Carl Zeiss, Germany) without washing the cells.

Figure 6:
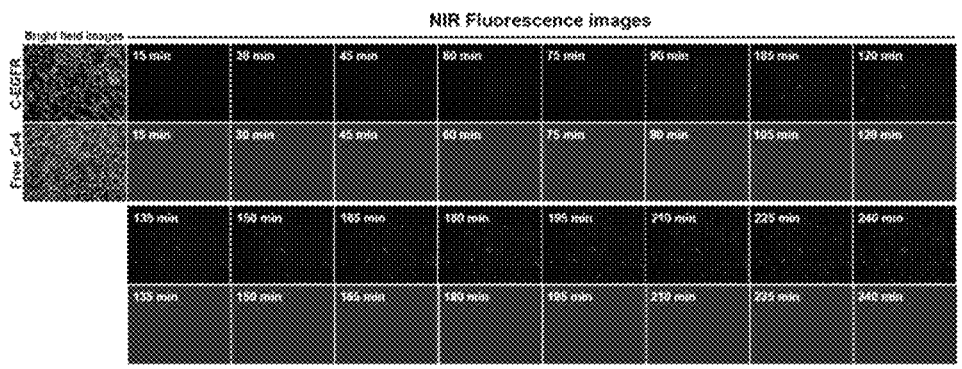
FIG. 6 is a photograph of a C-EGFR and a free dye Ce4 of Example 2 of the present invention treated on HCC70 cells, followed by near-infrared fluorescence imaging with no washing process in each time period ($\lambda_{Ex.}$ 640±15 nm, $\lambda_{Em}$ 690±25 nm).

According to FIG. 6, it can be understood that when the C-EGFR conjugate is treated, fluorescence signal generation is inhibited from outside the cell, and after the conjugate binds to the EGFR present on the cell surface, the strong fluorescent signal is generated after being absorbed into cells, and the position of each cell can be confirmed from the fluorescence image. This indicates that the quenching effect is terminated as the conjugate, which has been quenched outside the cell, is degraded via a disulfide bond in the cell, and from this time on, a bright fluorescent signal is generated. On the other hand, in the case of treatment with free photosensitizer, since the generation of fluorescence signal is always activated, it can be understood that the position of cancer cells cannot be distinguished from the fluorescence image due to the high background signal caused by strong fluorescence signal generated outside the cell.

6) Specific Cell Absorption and Fluorescence Activity of the Conjugate Accordingly PCA-SMC cells and HCC70 cells per well were put in an 8-well Lab-Tek chamber, PCA-SMC cells were put at a cell number of $5 \times 10^3$ in each well, and HCC70 cells were put at a cell number of $5 \times 10^4$ in each well, and were cultured for 24 hours to allow the cells to be absorbed well. Thereafter, the existing medium was replaced with 200 μl of fresh medium in which the C-EGFR conjugate (2 μM) was dissolved, and then the cells were cultured for 4 hours.

Finally, the cells were washed three times with the culture medium, and then a near-infrared fluorescence image ($\lambda_{Ex}$ 405 nm, $\lambda_{Em.}$ 625~754 nm) was obtained using a confocal laser microscope (CLSM, ZEISS LSM 510 META, Germany).

Experiments were performed to determine the intracellular location of the C-EGFR conjugate of the present invention. In the 8-well Lab-Tek chamber, $5 \times 10^3$ PCA-SMC cells and $5 \times 10^4$ HCC70 cells were put in each well. The cells were cultured for 24 hours to allow the cells to be absorbed well, and then 2 μM C-EGFR was added and cultured for 4 hours, followed by washing three times. Thereafter, after replacing the existing medium with fresh medium including 100 nM LysoTracker Blue DND-22 dye, the cells were cultured for 45 minutes. Fluorescent images of the C-EGFR conjugate ($\lambda_{Ex}$ 405 nm, $\lambda_{Em.}$ 625~754 nm) and LysoTracker ($\lambda_{Ex.}$ 405 nm, $\lambda_{Em.}$ 411~497 nm) were obtained for these samples using confocal microscopy.

Figure 7:
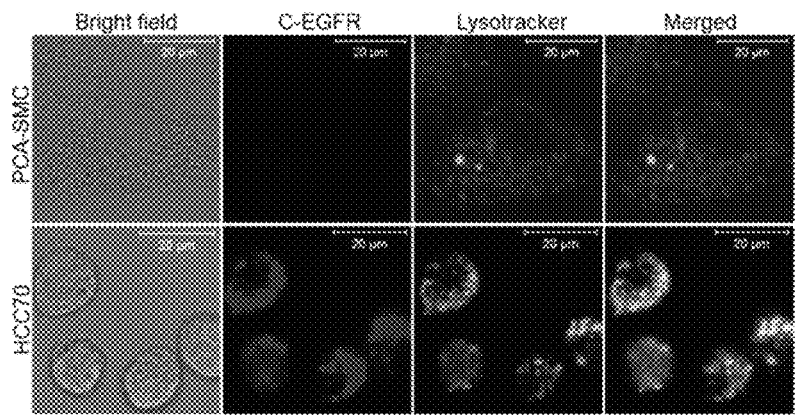
FIG. 7 is a fluorescence graph of a C-EGFR of Example 2 of the present invention treated on PCA-SMC, a normal cell line, and HCC70, a human breast cancer cell line, for 4 hours, respectively, followed by additional treatment of Lysotracker for lysosomal staining using a confocal laser microscope (CLSM) ($\lambda_{Ex.}$ 405 nm, $\lambda_{Em.}$ 625~754 nm).

According to FIG. 7, it was confirmed that when the C-EGFR conjugate was treated on HCC70 cells, strong fluorescence signals were exhibited after absorption into cells, and fluorescence signals were hardly exhibited when the conjugate was treated on PCA-SMC cells. This result supports that the C-EGFR conjugate was absorbed into cells by specific interaction with EGFR on the surface of HCC70 cells, which is an EGFR-overexpressing cell. In addition, when Lysotracker, which specifically stains lysosomes in cells, was treated together with a conjugate, it was confirmed that there was a site to be stained jointly. Even when the fluorescence images appear to overlap, the positions are exactly overlapping, and thus the C-EGFR conjugate migrated into the lysosomes with a high glutathione concentration inside the cells, indicating that the fluorescence activation occurred here.

7) Cytotoxicity and Photodynamic Therapy Efficacy Experiment

Figure 8A:
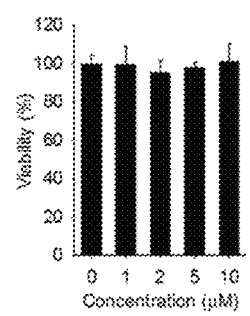
FIG. 8A is data of the cell survival rate obtained by treating HCC70, a human breast cancer cell line with various concentrations of C-EGFR, in order to analyze the cytotoxicity against the C-EGFR of Example 2.

In the dark state without light, the C-EGFR conjugate of the present invention was treated with 0~10 μM concentration in HCC70 cells and cytotoxicity was evaluated. As a result, as illustrated in FIG. 8A, it was confirmed that when the light was not irradiated, it did not show cytotoxicity in the corresponding concentration range.

In order to evaluate the effect of target photodynamic therapy, PCA-SMC cells were put in a $1 \times 10^3$/well and HCC70 cells were put in a $1 \times 10^4$/well in a 96-well plate, and were cultured for 24 hours to allow the cells to be adhered well. C-EGFR conjugates were prepared at concentrations of 0.1 μM, 0.5 μM, 1 μM, 2 μM, 5 μM and 10 μM, respectively, treated with cells, and then cultured for 4 hours. Thereafter, the C-EGFR conjugate that had not been introduced into the cells was washed and removed, and then irradiated with a 670 nm laser at an irradiation dose density of 50 mW/cm$^2$ for 6 minutes and 40 seconds. Thereafter, after culturing in an incubator overnight for stabilization, the cytotoxicity was assessed by CCK-8 assay.

Figure 8B:
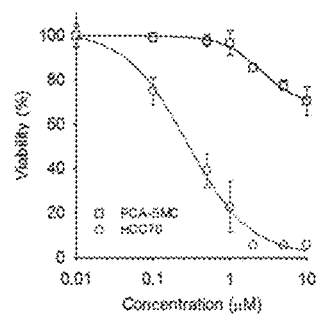
FIG. 8B is data that analyses the cell survival rate obtained by treating PCA-SMC cells and HCC70 cells with various concentrations for 4 hours and washing the same in order to verify the effect of the target cell-specific photodynamic therapy on the C-EGFR of Example 2, followed by irradiation of 670 nm laser to perform photodynamic therapy.

As a result, according to FIG. 8B, the IC$_{50}$ value of the C-EGFR conjugate in HCC70 cells was calculated to be 0.28 μM, and in PCA-SMC cells, it was confirmed that at least 70% of the cells were alive even at a high concentration of 10 μM. Therefrom, it can be understood that the C-EGFR conjugate is absorbed into cancer cells via EGFR as a medium, and the fluorescence and photodynamic therapy effects are activated, leading to a high cancer therapeutic effect even at low concentrations.

[Example 3] Preparation and Characteristic Analysis of Photosensitizer-Peptide Conjugates (L-EGFR) Including Linear Disulfide Bond Linkers In Example 3, the linker between the photosensitizer and the tryptophan was linear, and it was verified that the fluorescence and reactive oxygen generation, which were quenched when the linear linker degraded in the cells, was activated. To this end, Ce4 was selected as a photosensitizer, and conjugates of GE11 peptide including tryptophan (YHWYGYTPQNVI) and a photosensitizer linked via a linear disulfide bond were synthesized and analyzed for their efficacy.

3.1. Synthesis of a Photosensitizer-Peptide Conjugate (L-EGFR) Including Linear Disulfide Bond Linkers The peptides were prepared by Fmoc solid phase peptide synthesis method using ASP48S, and the preparation process was provided as follows.

Eight equivalents of Fmoc-miniPEG2-OH and eight equivalents of HBTU/eight equivalents of HOBt/16 equivalents of NMM were dissolved in DMF and were added to H-Cys(Trt)-2-chloro-Trityl resin (Anaspec, USA) and reacted at room temperature for 2 hours, followed by washing with DMF, methanol and DMF in that orderly manner.

In order to isolate the protecting group Fmoc attached to the amino acid, DMF including 20% piperidine was added to the reaction solution and reacted twice at room temperature for 5 minutes, followed by washing with DMF, methanol and DMF in that orderly manner.

Four equivalents of chlorin e4(Ce4) and four equivalents of HBTU/four equivalents of HOBt/eight equivalents of NMM were dissolved in DMSO and added to the peptide resin for reaction for 12 hours and suction. The resulting Ce4-miniPEG2-Cys(Trt)-2-chloro-Trityl resin was washed with methanol and DMF in that orderly manner.

The resulting peptide resin was treated with a solution of TFA/EDT/thioanisole/TIS/water diluted to 90/2.5/2.5/2.5/2.5 to remove the protecting group of the peptide residue and isolate the peptide from the resin to obtain Ce4-miniPEG2-Cys.

Thereafter, 10 times of cold diethyl ether was added to the reaction solution to precipitate the peptide, and centrifugation was carried out at 3000 rpm for 10 minutes. The filtrate was discarded and repeated twice. The conjugate thus obtained was purified by reverse phase HPLC.

The Ce4-miniPEG2-Cys and Aldrithiol-2 thus obtained were dissolved in acetic acid and reacted at room temperature for 4 hours. The progress of the reaction was confirmed by HPLC and LC/MS. When the reaction was completed, the reaction mixture was centrifuged and purified to obtain lyophilized Ce4-miniPEG-Cys(Pys).

On the other hand, for the peptide scaffold synthesis, eight equivalents of Fmoc-amino acid and eight equivalents of HBTU/eight equivalents of HOBt/16 equivalents of NMM were dissolved in DMF and were added to H-Ile-2-chloro-Trityl resin (Anaspec, USA) and reacted at room temperature for 2 hours, followed by washing with DMF, methanol and DMF in that orderly manner.

In order to isolate the protecting group Fmoc attached to the amino acid, DMF including 20% piperidine was added to the reaction solution and reacted twice at room temperature for 5 minutes, followed by washing with DMF, methanol and DMF in that orderly manner.

This process was repeated to synthesize a resin-bound structure on the peptide basic scaffold [H-Cys(Trt)-Tyr(t-Bu)-His(Trt)-Trp(Boc)-Tyr(t-Bu)-Gly-Tyr(t-Bu)-Thr(t-Bu)-Pro-Gln(Trt)-Asn(Trt)-Val-Ile-2-chloro-Trityl Resin].

The resulting peptide resin was treated with a solution of TFA/EDT/thioanisole/TIS/water diluted to 90/2.5/2.5/2.5/2.5 to remove the protecting group of the peptide residue and isolate the peptide from the resin.

Thereafter, 10 times of cold diethyl ether was added to the reaction solution to precipitate the peptide, and centrifugation was carried out at 3000 rpm for 10 minutes. The filtrate was discarded and repeated 2 times. The conjugate thus obtained was purified by reversed phase HPLC.

The purified peptide scaffold and Ce4-miniPEG2-Cys (Pys) were dissolved in a 1:1 solution of water and acetonitrile and reacted at room temperature for 12 hours. The progress of the reaction was confirmed by HPLC and LC/MS. After confirming the completion of the reaction, the reaction mixture was purified by reversed phase HPLC. Elution was performed using a water-acetonitrile linear gradient using a 40 to 70% (v/v) acetonitrile solution including TFA 0.1%.

The chemical structure of the L-EGFR conjugate thus prepared is shown in the following Formula 2. That is, the photosensitizer and the EGFR target peptide were bound via a linear disulfide bond.

[Formula 2]

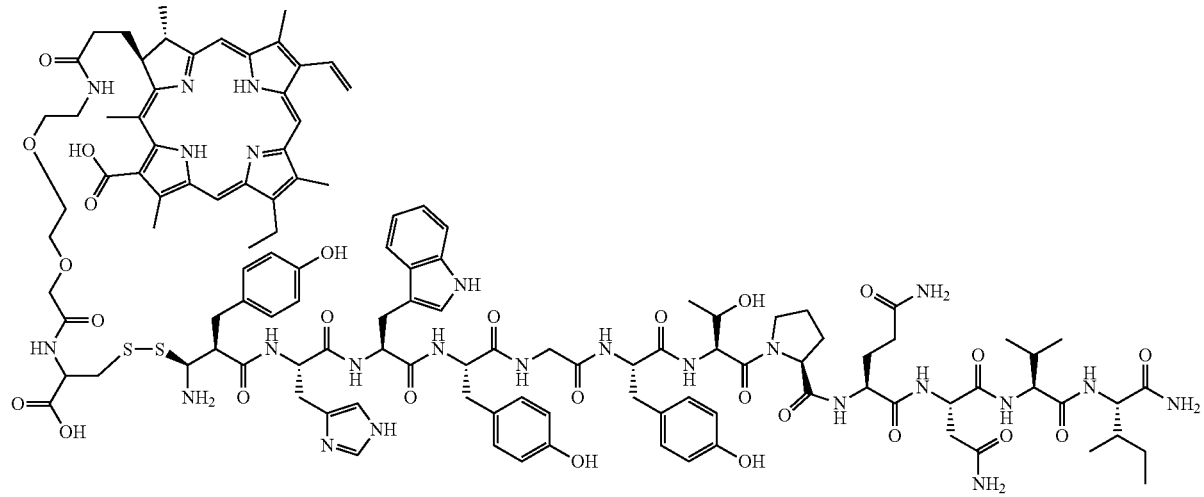

3.2. Characteristics of a Linear L-EGFR Conjugate

1) Molecular Weight and Absorption Spectrum

The molecular weight was measured using LC/MSD and the absorbance was measured using a UV/Vis spectrometer.

Figure 9:
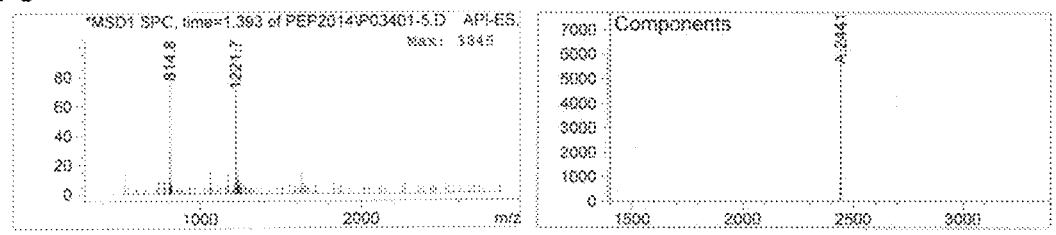
FIG. 9 is mass spectrometry data of an L-EGFR which is a photosensitizer-peptide conjugate including a linear disulfide bond linker synthesized in Example 3 of the present invention.
Figure 10A:
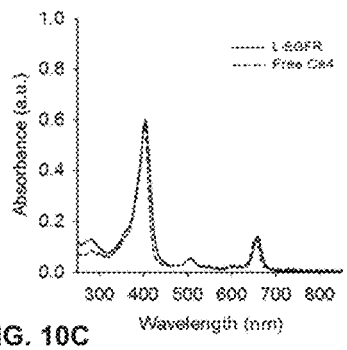
FIG. 10A is data illustrating UV/Vis absorption spectra of a free dye Ce4 and an L-EGFR, a photosensitizer-peptide conjugate including a linear disulfide bond linker synthesized in Example 3.

As a result of the evaluation, the molecular weight of Formula 2 of the purified conjugate of the present invention thus obtained was 2,441 g/mol (FIG. 9) and the maximum absorption peaks were shown at 282, 404, 505 and 660 nm, respectively, on the absorption spectrum (see FIG. 10A).

2) Analysis of Fluorescence and Reactive Oxygen Generation Recovery by Reducing Agent Action Fluorescence recovery of the conjugate thus obtained by the reaction in response to a reducing agent present in a high concentration in cancer cells was performed and analyzed in the same manner as in Example 2. On the other hand, a sample prepared by dilution was put into a multifunctional microplate reader to obtain fluorescence spectrum ($\lambda_{Ex.}$ 400 nm, $\lambda_{Em.}$ 620~850 nm) results.

In addition, in order to confirm the generation of singlet oxygen (SOG), the same method as in Example 2 was performed and analyzed.

Figure 10B:
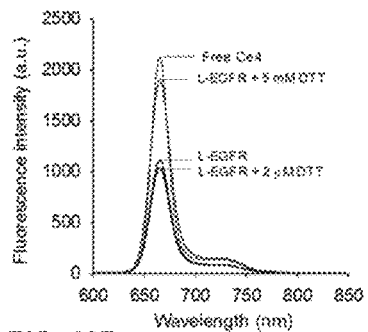
FIG. 10B is a fluorescence spectrum obtained after treating the L-EGFR conjugate of Example 3 with a phosphate-buffered saline (PBS) solution, DTT at 2 µM and 5 mM for 4 hours ($\lambda_{Ex.}$ 400 nm; For comparison, the fluorescence spectrum for the same concentration of free dye Ce4 is shown).
Figure 10C:
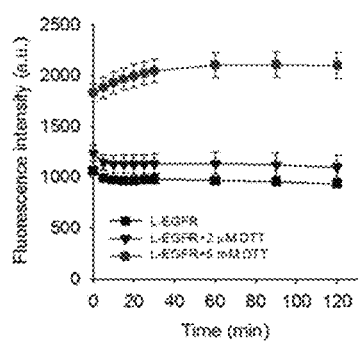
FIG. 10C is data obtained by treating the L-EGFR conjugate of Example 3 with a PBS solution, DTT at 2 µM and 5 mM, and then measuring the change in fluorescence intensity with time ($\lambda_{Ex.}$ 400 nm, $\lambda_{Em.}$ 665 nm).
Figure 10D:
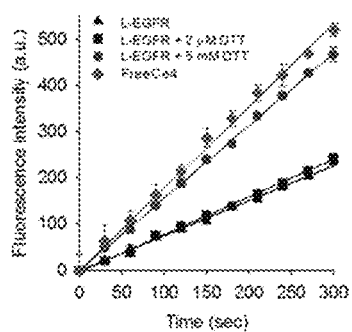
FIG. 10D is a graph that analyses the generation of singlet oxygen by treating the L-EGFR conjugate of Example 3 with a PBS solution, DTT at 2 µM and 5 mM for 4 hours, respectively, and irradiating a 670 nm laser.

According to FIG. 10, it was confirmed that fluorescence was not generated when only the L-EGFR conjugate was present (OFF state), and the fluorescence intrinsic to the photosensitizer was exhibited when liner disulfide linkers were degraded during 5 mM DTT treatment (ON state) (FIG. 10B). It was confirmed that fluorescence intensities of fluorescence expression state (ON) increased 2.5 times compared to the quenching (OFF) state, and that the fluorescence of the free photosensitizer was almost recovered. In particular, it can be understood that at least 90% of the fluorescence is rapidly recovered within 5 minutes after the start of the reaction (FIG. 10C).

In addition, in the quenching state, the generation of singlet oxygen was suppressed, and in the case of 5 mM DTT treatment, the quenching state was terminated and the generation of singlet oxygen was increased 2 times. Therefore, it can be understood that L-EGFR of Example 3 of the present invention activates fluorescence and singlet oxygen generation as the disulfide bond breaks upon absorption into target cells.

3) Serum Stability

The L-EGFR conjugate of the present invention was mixed with PBS including 10% of PBS, fetal bovine serum (FBS, Gibco, USA), respectively, and cultured, and the stability in the serum was evaluated. The final concentration of the conjugate in solution was adjusted to 2 µM. The solution was allowed to react at room temperature for 4 hours and then put in a multifunctional microplate reader (Safire 2, Tecan, Switzerland) to obtain a fluorescence spectrum ($\lambda_{Ex.}$ 400 nm) result.

Figure 11:
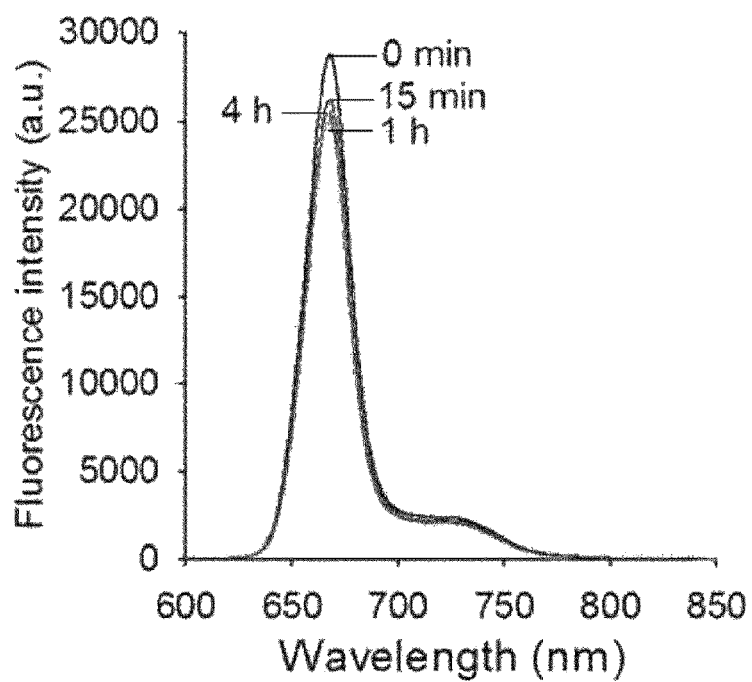
FIG. 11 is a result of measuring fluorescence changes in each time period by dissolving RedoxT in a phosphate-buffered aqueous solution including serum, in order to observe whether the fluorescence quenching effect is stably maintained under the condition that the L-EGFR conjugate of Example 3 is present in serum.
Figure 15A:
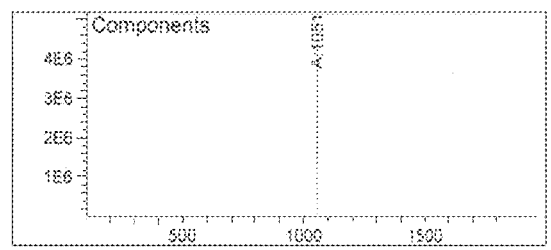
FIG. 15A is mass spectrometry data of Ce4-RRW as a photosensitizer-peptide conjugate of Example 4 of the present invention.
Figure 15B:
FIG. 15B is mass spectrometry data of Ce4-RRWW as a photosensitizer-peptide conjugate of Example 4 of the present invention.
Figure 15C:
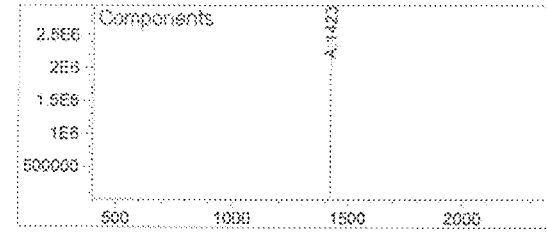
FIG. 15C is mass spectrometry data of Ce4-RRWWW as a photosensitizer-peptide conjugate of Example 4 of the present invention.
Figure 15D:
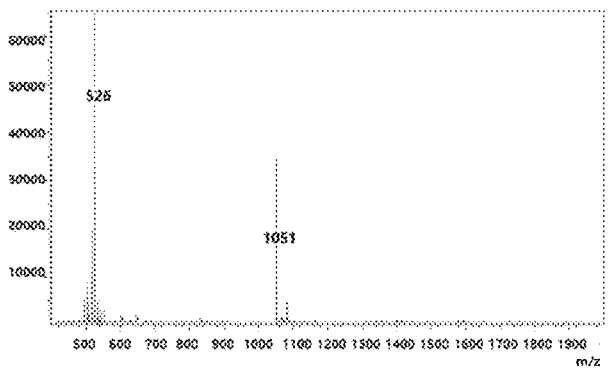
FIG. 15D is mass spectrometry data of Ce4-RWR as a photosensitizer-peptide conjugate of Example 4 of the present invention.

According to FIG. 11, it was confirmed that the serum protein did not affect the fluorescence intensity of the conjugate.

4) Cell Culturing

The human breast cancer cell line MDA-MB-468 overexpressing epithelial growth factor receptor (EGFR), the moderately expressing MDA-MB-231 and the human normal cell line PCA-SMC not expressing EGFR were all obtained from the American Type Culture Collection (ATCC, USA).

The MDA-MB-231 cells were cultured in RPMI (Roswell Park Memorial Institute) 1640 medium including 10% fetal bovine serum and 1% penicillin/streptomycin (Life Technologies) at 37° C. under 5% carbon dioxide and standard humidity conditions. The MDA-MB-468 cells were cultured in DMEM (Dulbecco's modified Eagle's medium) including 10% FBS and 1% penicillin/streptomycin (Life Technologies) at 37° C. under 5% carbon dioxide and standard humidity conditions. PCA-SMC cells were cultured in vascular cell basal medium including recombinant human insulin, ascorbic acid, glutamine, recombinant human epithelial growth factor, and FBS 10% at 37° C. under 5% carbon dioxide and standard humidity conditions.

5) Immunocytochemical Analysis

The expression level of EGFR, a target protein, in each cell was measured by immunocytochemistry. PCA-SMC, MDA-MB-231 and MDA-MB-468 cells were attached to the cover glass and immobilized with PBS including 4% paraformaldehyde for 15 minutes at room temperature and washed twice. Immobilized cells were reacted with 0.25% triton X-100 for 10 minutes and washed three times with PBS for 5 minutes. Thereafter, PBST buffer solution including 1% BSA (Bovine serum albumin) was treated in cells for 30 minutes, and then reacted with EGFR antibody (1:500 dilution) for 1 hour, and then washed three times with PBS for 5 minutes. Thereafter, the cells were reacted with secondary antibody (1:500 dilution) in the dark for 1 hour and then washed three times with PBS for 5 minutes. A cell nucleus was stained with DAPI for 1 minute, washed with PBS and mounted.

According to FIG. 12A, MDA-MB-468 cell line showed high EGFR expression, MDA-MB-231 cell line showed moderate EGFR expression, and PCA-SMC showed very low EGFR expression.

6) Intracellular Absorption of a Conjugate and the Resulting Fluorescence Activity PCA-SMC, MDA-MB-231 and MDA-MB-468 cells were put in each well of an 8-well Lab-Tek chamber, PCA-SMC cells were put, in each well, at a cell number of $5 \times 10^3$, and MDA-MB-231, MDA-MB-468 cells were put, in each well, at a cell number of $5 \times 10^4$, and were cultured for 24 hours to allow the cells to be adhered well. Thereafter, the existing medium was replaced with 200 µl of a fresh medium in which 2 µM the conjugate was dissolved, and the cells were cultured for 30 minutes, 1 hour, and 4 hours, respectively.

Finally, the cells were washed three times with fresh culture medium to remove the conjugate present outside the cells, and a near-infrared fluorescence image ($\lambda_{Ex.}$ 405 nm, $\lambda_{Em.}$ 625~754 nm) was obtained using a confocal laser microscope.

Experiments were performed to determine the intracellular location of the L-EGFR conjugate of the present invention. $1 \times 10^5$ cells per well were put in an 8-well Lab-Tek chamber and cultured for 24 hours to allow the cells to be absorbed well. L-EGFR conjugate was treated at a concentration of 2 µM and was cultured for 4 hours, followed by washing three times. To stain the lysosomes, the existing medium was replaced with fresh medium including 100 nM LysoTracker Blue DND-22 dye, and the cells were cultured for 45 minutes. As to the sample, fluorescence images were obtained for the conjugate ($\lambda_{Ex.}$ 405 nm, $\lambda_{Em.}$ 625~754 nm) and LysoTracker ($\lambda_{Ex.}$ 405 nm, $\lambda_{Em.}$ 411~497 nm) using a confocal microscope.

According to FIG. 12B, it was confirmed that when the L-EGFR conjugate was treated on PCA-SMC cells, it did not enter the cell even after culturing for 4 hours. When the expression level of EGFR on the cancer cell surface was high, the cell absorption was increased. It can be understood that in the case of MDA-MB-231 cells, fluorescence was almost not observed when cultured for the first 30 minutes, but fluorescence intensity was increased with increasing culture time. On the other hand, MDA-MB-468 cells showed a strong fluorescence signal on the cell surface even if cultured for a short period of 30 minutes, and were found to enter the cell as culture time increased. This result supports that the L-EGFR conjugate of Example 3 was absorbed into cells via a specific interaction with EGFR on the cell surface.

According to FIG. 13, when a Lysotracker specifically straining a lysosome in a cell was stained together with a conjugate, it was confirmed that there was a site stained jointly. Even when the fluorescence images were superimposed on each other, the position looked superimposed exactly. It was confirmed that the L-EGFR conjugate was located in a high concentration of glutathione, a reducing agent, in the cell lysosome, and was activated in the lysosome.

7) Cytotoxicity and Photodynamic Therapy Efficacy Experiment

In the dark state without light, the L-EGFR conjugate of the present invention was added to MDA-MB-468 cells at a concentration of 0~10 µM and cytotoxicity was evaluated. As a result, as illustrated in FIG. 14A, it was confirmed that when the light was not irradiated, it did not show cytotoxicity in the corresponding concentration range.

In order to evaluate the efficacy of photodynamic therapy, PCA-SMC cells were put in a $1 \times 10^3$/well and MDA-MB-231 cells and MDA-MB-468 cells were put as much as $1 \times 10^4$/well in a 96-well plate, respectively, and were cultured for 24 hours to allow the cells to be adhered well. L-EGFR conjugates were prepared at concentrations of 0.1 µM, 0.5 µM, 1 µM, 2 µM, 5 µM and 10 µM, respectively, treated with cells, and then cultured for 4 hours. Thereafter, the conjugate that had not been absorbed into cells was washed and removed, and then irradiated with a 670 nm laser at an irradiation dose density of 50 mW/cm² for 6 minutes and 40 seconds. Thereafter, after further culturing in an incubator until the next day, the cytotoxicity was assessed by CCK-8 assay.

As a result, according to FIG. 14B, the $IC_{50}$ value of the conjugate in MDA-MB-468 cells was calculated to be 0.66 µM and 1.81 µM in MDA-MB-231 cells. In the PCA-SMC cells, it was confirmed that at least 70% of the cells were alive even at a high concentration of 10 µM. Therefrom, it can be understood that the L-EGFR conjugate is absorbed into cancer cells via EGFR as a medium, and that the conjugate thus absorbed induces a high cancer therapeutic effect even at a low concentration.

[Example 4] Preparation and Characteristic Analysis of a Peptide Conjugate Including Photosensitizer-Arginine and Tryptophan 4.1. Preparation of a Conjugate Including a Photosensitizer, Arginine and Tryptophan The peptides were prepared by Fmoc solid phase peptide synthesis (SPPS) using ASP48S. The preparation process is provided as follows.

The amino acid with the protecting group (Fmoc) bound to Trt-Cl resin (GL Biochem, China) was strongly mixed with DMF including 20% piperidine and reacted twice at room temperature for 10 minutes, followed by washing with DMF and methanol twice. Thereafter, eight equivalents of amino acid and eight equivalents of HBTU/eight equivalents of HOBt/16 equivalents of N,N-Diisopropylethylamine (DIPEA) were dissolved in DMF and added, and reacted at room temperature for 2 hours, followed by washing with DMF and methanol twice. This process was repeated to make RRW-resin, RRWW-resin, RRWWW-resin and RWR-resin, respectively.

The photosensitizer Ce4 and HBTU/HOBt/DIPEA were dissolved in DMF and added to the resin-peptide basic scaffold conjugate, and then the mixed solution was reacted for 12 hours and suctioned, followed by washing with DMF, methanol and DMF in that orderly manner.

When the peptide scaffold to be synthesized is formed through this process, a solution in which TFA/EDT/thioanisole/TIS/water was diluted with 90/2.5/2.5/2.5/2.5 was treated for 2 hours. The protecting group of the peptide residue thus prepared was removed and the peptide was isolated from the resin. Thereafter, cold diethyl ether was added to the reaction solution to precipitate the peptide, centrifugation was carried out, and the obtained product was dried.

The finally obtained product was dissolved in DMSO and purified by reverse phase HPLC using a Vydac Everest C18 column (250 mm×22 mm×10 µm, USA). Elution was performed using a water-acetonitrile linear gradient using 10 to 75% (v/v) acetonitrile solution including TFA 0.1%, and the purified product was lyophilized.

The chemical structure of the prepared conjugate (Example 4) prepared as above is as shown in the following Formulas 3 to 6, and the photosensitizer and tryptophan are linked via arginine.

[Formula 3]

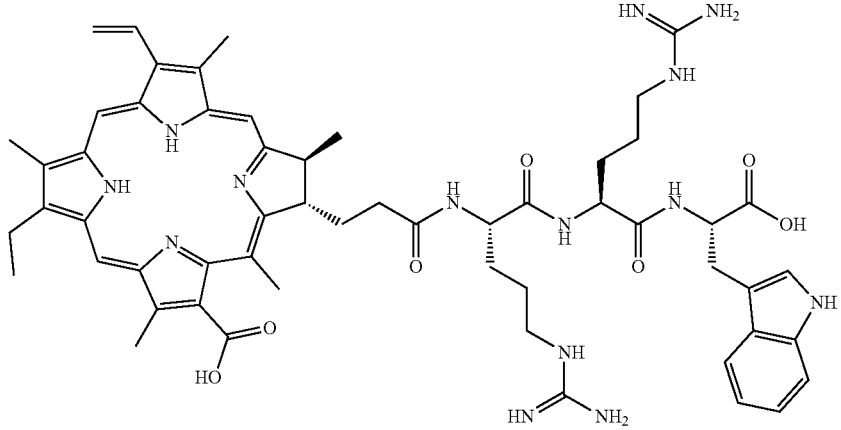

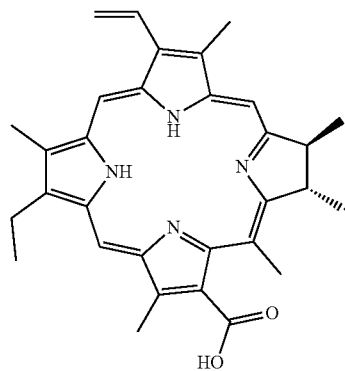
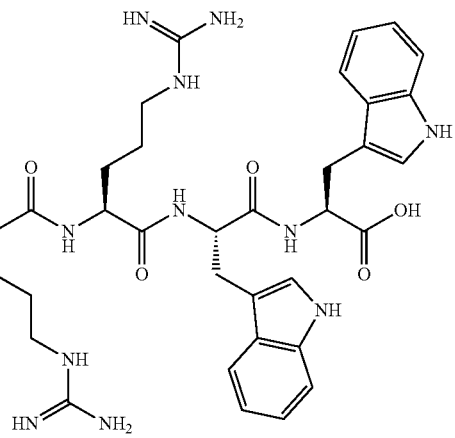

[Formula 4]

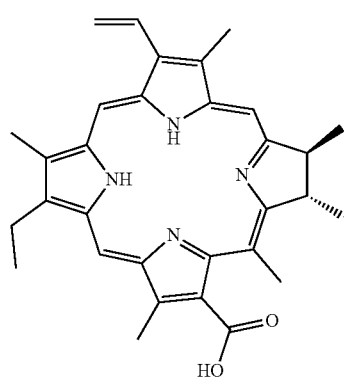
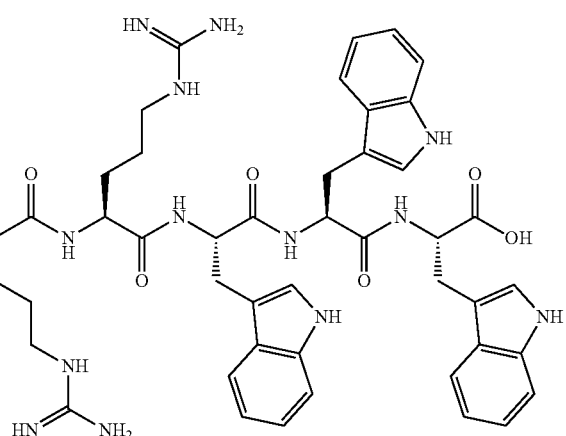

[Formula 5]

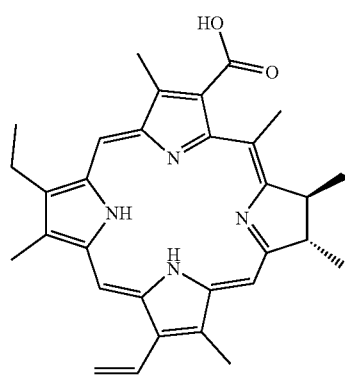
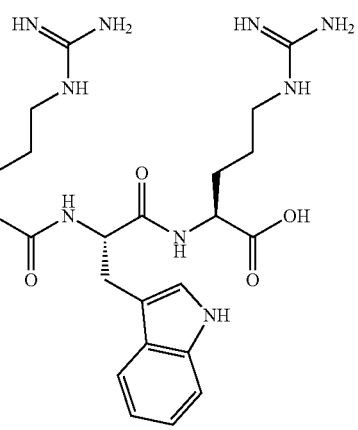

[Formula 6]

4.2. Characteristics of a Conjugate Including a Photosensitizer, Arginine, Tryptophan 1) Molecular Weight and Fluorescence Emission The molecular weight was measured using LC/MSD and the absorbance was measured using a UV/Vis spectrometer.

Figure 16A:
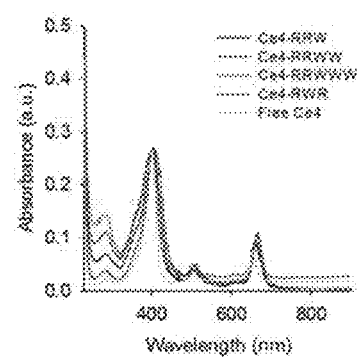
FIG. 16A is UV/Vis absorption spectrum data of Ce4-RRW, Ce4-RRWW, Ce4-RRWWW, Ce4-RWR and free dye Ce4 of Example 4 of the present invention.
Figure 16B:
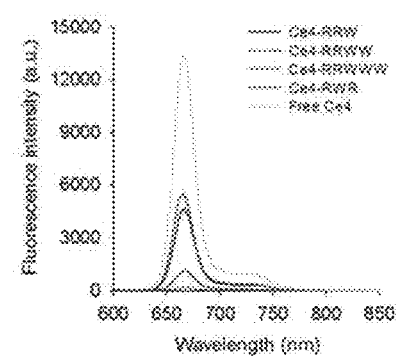
FIG. 16B is fluorescence spectrum ($\lambda_{Ex.}$ 400 nm) data of Ce4-RRW, Ce4-RRWW, Ce4-RRWWW, Ce4-RWR and free dye Ce4 of Example 4 of the present invention.

As a result of the evaluation, the molecular weight of the purified conjugate of the present invention thus obtained was measured to be 1,051 g/mol for Ce4-RRW, 1,237 g/mol for Ce4-RRWW, 1,423 g/mol for Ce4-RRWWW, 1,051 g/mol for Ce4-RWR, respectively (see FIG. 15), and exhibited maximum absorption and maximum emission at 403~404 nm and 666~668 nm, respectively (see FIGS. 16A and 16B).

2) Increase in Fluorescence Signal Due to Enzyme Action 1 nmol of each of Ce4-RRWW and Ce4-RRWWW thus obtained was prepared and dissolved in a PBS solution. The trypsin enzyme was mixed with each 50 nmol of each conjugate and fluorescence changes were observed over time at 37° C.

Figure 17:
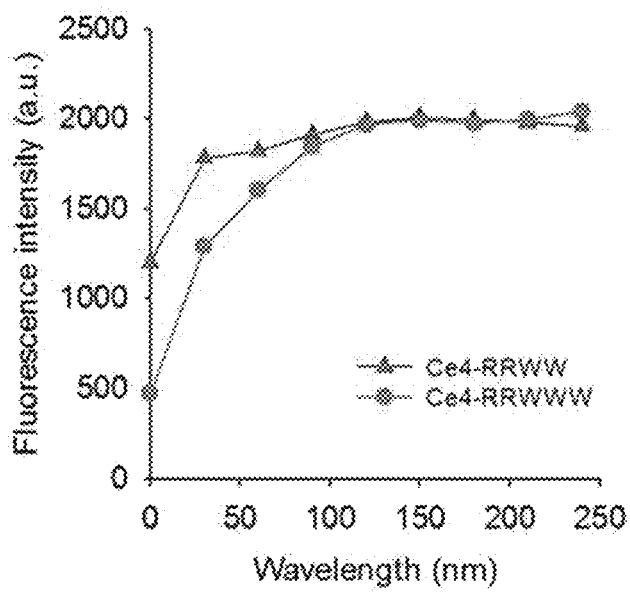
FIG. 17 is a graph ($\lambda_{Ex.}$ 400 nm) that observes the fluorescence increase with time at 665 nm after treating Ce4-RRWW and Ce4-RRWWW of Example 4 of the present invention with trypsin enzyme, respectively.

According to FIG. 17, it was observed that fluorescence was recovered in both conjugates after treatment with trypsin enzyme. After 4 hours, the fluorescence of Ce4-RRWW was increased by about 1.6 times, and that of Ce4-RRWWW was increased by 4.3 times, respectively, than that of the initial fluorescence.

The Ce4-RRW thus obtained was diluted in 93.5 μl of sodium acetate buffer (20 mM sodium acetate buffer, 1 mM EDTA, pH 5.0), and then 97 pmol of cathepsin B (Calbiochem, USA) was mixed in the enzyme-treated sample. The same amount of sodium acetate buffer solution was mixed in the buffer solution-treated group. The mixed solution (1000 was cultured at 37° C. for 2 hours.

3) Serum Stability

The Ce4-RRW conjugate of the present invention was mixed with PBS including 10% of FBS and cultured to evaluate the stability in serum. The final concentration of the conjugate in solution was adjusted to 2 μM. The solution was allowed to react at room temperature for 4 hours and then put in a multifunctional microplate reader to obtain a fluorescence spectrum ($\lambda_{Ex.}$ 610 nm, $\lambda_{Em.}$ 620~850 nm) result.

Figure 18:
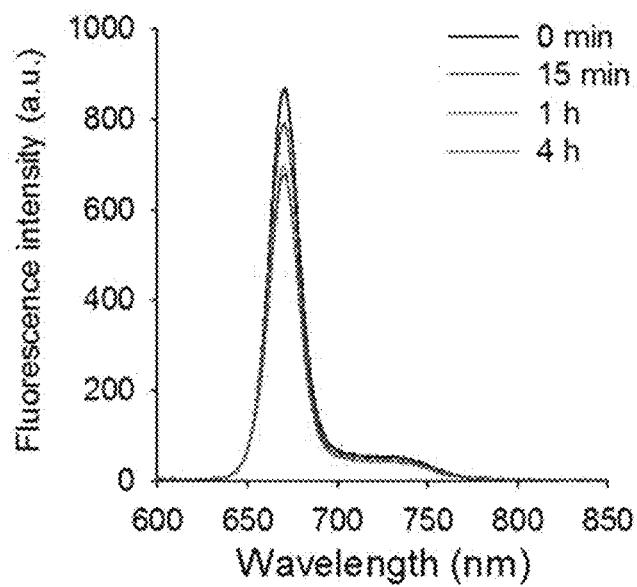
FIG. 18 is a graph measuring the stability in the serum by measuring the change of fluorescence in each time period after dissolving Ce4-RRW as a photosensitizer-peptide conjugate of Example 4 of the present invention in a phosphate-buffered saline (PBS) including the serum.

According to FIG. 18, it was confirmed that the serum protein did not affect the fluorescence of Ce4-RRW.

4) Cell Culturing

Human cancer KB cell line was obtained from ATCC. The KB cells were cultured in MEM (Minimum Essential Media) medium (Gibco) including 10% FBS and 1% penicillin/streptomycin at 37° C. under 5% carbon dioxide condition.

5) Specific Cell Absorption and Fluorescence Activity of the Conjugate Accordingly KB cells per well were put in a 4-well Lab-Tek chamber per 2×10$^5$, and were cultured for 24 hours to allow the cells to be absorbed well. Thereafter, the existing medium was replaced with 500 μl of fresh medium in which the Ce4-RRW conjugate (2 μM) was dissolved, and then the cells were cultured for 4 hours.

Finally, the cells were washed three times with the culture medium, and then a near-infrared fluorescence image ($\lambda_{Ex.}$ 405 nm, $\lambda_{Em.}$ 625~754 nm) was obtained using a confocal laser microscope.

Experiments were performed to determine the intracellular location of the Ce4-RRW of the present invention. In the 8-well Lab-Tek chamber, 5×10$^4$ KB cells were put in each well. The cells were cultured for 24 hours to allow the cells to be absorbed well, and then 2 μM Ce4-RRW was added and cultured for 4 hours, followed by washing three times. Thereafter, after replacing the existing medium with fresh medium including 100 nM LysoTracker Blue DND-22 dye, the cells were cultured for 45 minutes. Fluorescent images of the Ce4-RRW ($\lambda_{Ex.}$ 405 nm, $\lambda_{Em.}$ 625~754 nm) and LysoTracker ($\lambda_{Ex.}$ 405 nm, $\lambda_{Em.}$ 411~497 nm) were obtained for these samples using confocal microscopy.

Figure 19:
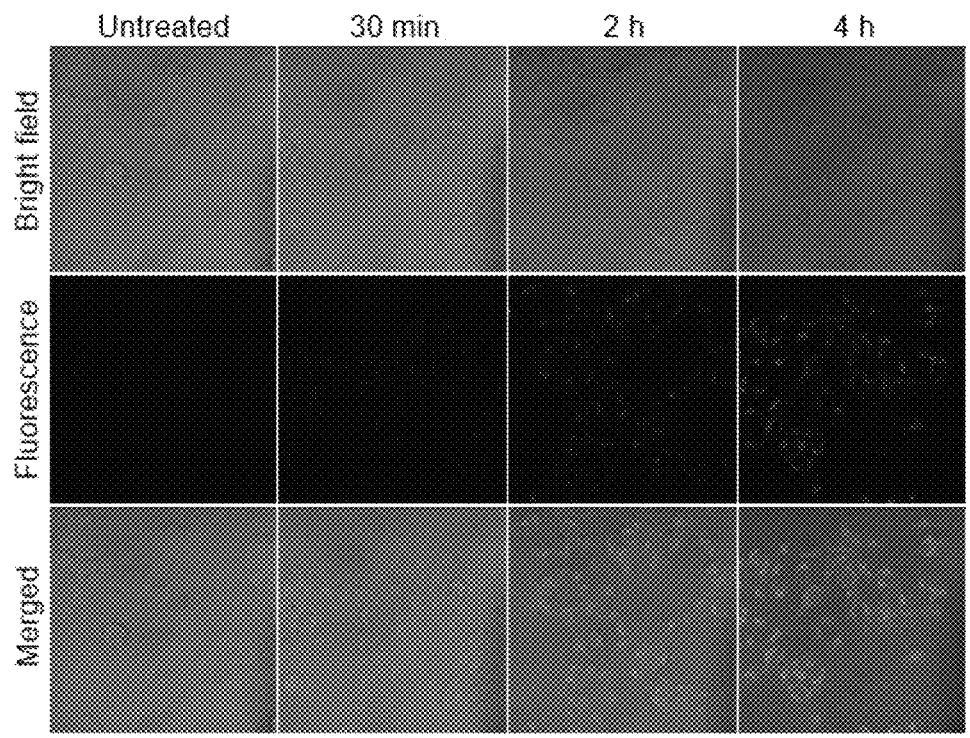
FIG. 19 is a confocal laser microscope photograph obtained by treating the conjugate with a KB cancer cell line for 30 minutes, 1 hour, 2 hours, and 4 hours, respectively, in order to analyze whether the Ce4-RRW, which is a photosensitizer-peptide conjugate of Example 4 of the present invention, exhibits fluorescence activation in cancer cells.

According to FIG. 19, when Ce4-RRW was treated on KB cells, it was introduced into cells and showed a strong fluorescence signal. In particular, when the Ce4-RRW of the present invention was treated, the intracellular fluorescence intensity was further increased with the lapse of culture time, and fluorescence generation was activated in target cells.

Figure 20:
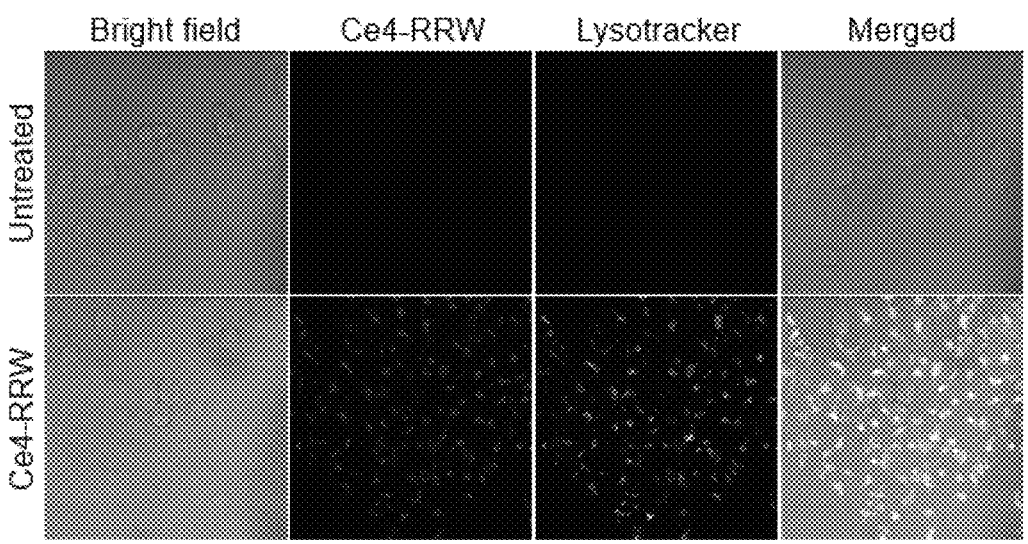
FIG. 20 is a confocal laser microscope photograph obtained by treating Ce4-RRW, which is a photosensitizer-peptide conjugate of Example 4 of the present invention, with KB cancer cell lines and further fluorescent staining of LysoTracker capable of staining intracellular lysosomes (It was confirmed that the lysosome having a high concentration of a reducing agent overlaps with the fluorescence of a photosensitizer. This indicates that the fluorescence activation occurs by the degradation of the conjugate by the reducing agent in the lysosome).

According to FIG. 20, when Lysotracker and Ce4-RRW specifically staining lysosomes in a cell were cultured together, it was confirmed that there was a site stained jointly. Even when the fluorescence images were superimposed on each other, the position looked superimposed exactly. It was confirmed that Ce4-RRW was located in the lysosome after absorption into cells and was activated by the enzyme.

[Example 5] Preparation of Photosensitizer-Peptide Conjugates Including Disulfide Bonds and Arginine In Example 5, when the photosensitizer, which had been quenched by tryptophan, was degraded by a complex action of an intracellular reducing agent and an enzyme, a strong fluorescence signal was generated while the quenching effect was terminated, and at the same time, a conjugate was prepared in which the photodynamic therapy efficacy was also recovered.

5.1. Synthesis of a Reducing Agent/Enzyme Complex Reaction Type Conjugate

The conjugate is a model of a conjugate having both a disulfide bond degraded by a reducing agent and a bond including arginine degraded by an enzyme, and Ce4-CRRCW conjugate was synthesized.

Peptides were prepared by Fmoc solid phase peptide synthesis (SPPS) using ASP48S. The preparation process is provided as follows.

The amino acid with the protecting group (Fmoc) bound to Trt-Cl resin (GL Biochem, China) was strongly mixed with DMF including 20% piperidine and reacted twice at room temperature for 10 minutes, followed by washing with DMF and methanol twice. Thereafter, eight equivalents of amino acid and eight equivalents of HBTU/eight equivalents of HOBt/16 equivalents of N,N-Diisopropylethylamine (DIPEA) were dissolved in DMF and added, and reacted at room temperature for 2 hours, followed by washing with DMF and methanol twice. This process was repeated to make CRRCW-resin.

The photosensitizer Ce4 and HBTU/HOBt/DIPEA were dissolved in DMF and added to the resin-peptide basic scaffold conjugate, and then the mixed solution was reacted for 12 hours and suctioned, followed by washing with DMF, methanol and DMF in that orderly manner.

When the peptide scaffold to be synthesized was formed through this process, a solution in which TFA/EDT/thioanisole/TIS/water was diluted with 90/2.5/2.5/2.5/2.5 was treated for 2 hours. The protecting group of the peptide residue thus prepared was removed and the peptide was isolated from the resin. Thereafter, cold diethyl ether was added to the reaction solution to precipitate the peptide, centrifugation was carried out, and the obtained product was dried.

The product obtained for cyclic disulfide bond generation was dissolved in a mixed solution of water/acetonitrile (9:1, v/v) at a concentration of 0.5 mg/mL, and ammonium acetate solution was added thereto and stirred (peptide solution:ammonium acetate=9:1, v/v). The progress of the reaction was confirmed by Elman reagent.

The finally obtained product was dissolved in DMSO and purified by reverse phase HPLC using a Vydac Everest C18 column (250 mm×22 mm×10 μm, USA). Elution was performed using a water-acetonitrile linear gradient using 10 to 75% (v/v) acetonitrile solution including TFA 0.1%, and the purified product was lyophilized.

The chemical structure of the conjugate Ce4-CRRCW prepared as above is as shown in the following Formula 7.

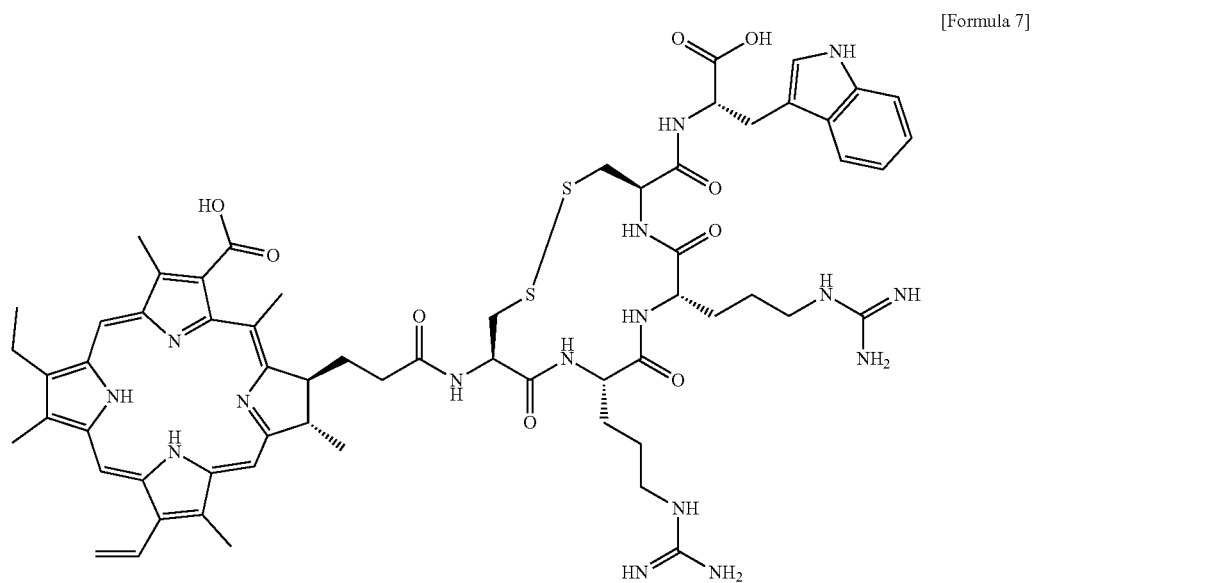 [SMILES: C=Cc1c(C)c2cc3nc(c(C)c4nc(cc5[nH]c(cc1[nH]2)c(C)c5CC)C(C)=C4C(=O)O)[C@@H](CCC(=O)N[C@H]1CSSC[C@@H](C(=O)N[C@@H](Cc2c[nH]c4ccccc24)C(=O)O)NC(=O)[C@H](CCCNC(=N)N)NC(=O)[C@H](CCCNC(=N)N)NC1=O)[C@@H]3C]

[Formula 7]

5.2. Characteristic Analysis of a Reducing Agent/Enzyme Complex Reaction Type Conjugate 1) Molecular Weight and Fluorescence Emission The molecular weight of the synthesized Ce4-CRRCW was measured using LC/MSD and the absorbance was measured using a UV/Vis spectrometer. The maximum absorption peaks were measured at 402, 508 and 665 nm.

Figure 21:
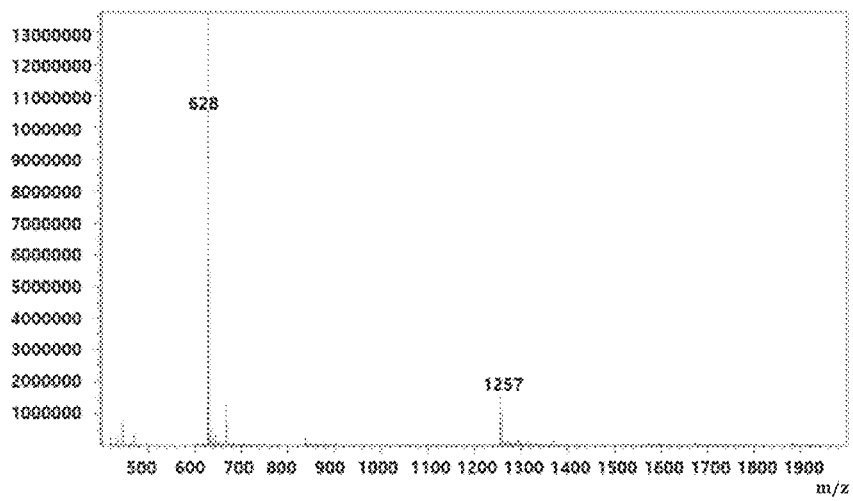
FIG. 21 is mass spectrometry data of Ce4-CRRCW, which is a photosensitizer-peptide conjugate of Example 5 of the present invention.
Figure 22A:
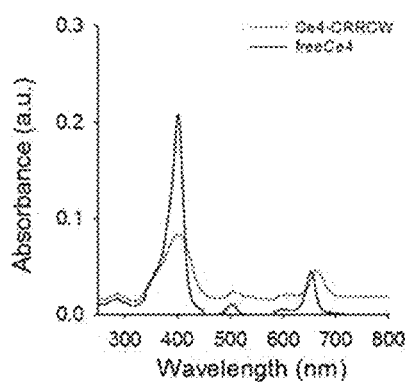
FIG. 22A is UV/Vis absorption spectrum data of Ce4-CRRCW, which is a photosensitizer-peptide conjugate of Example 5 of the present invention, and free dye Ce4.
Figure 22B:
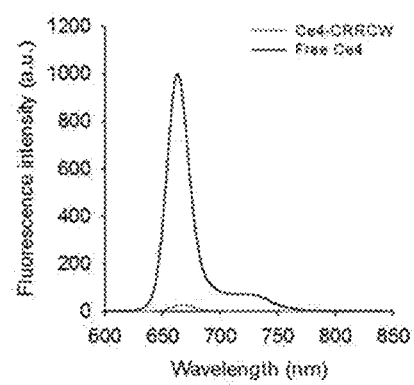
FIG. 22B is a fluorescence spectrum ($\lambda_{Ex.}$ 400 nm) of Ce4-CRRCW, which is a photosensitizer-peptide conjugate of Example 5 of the present invention, and free dye Ce4.

As a result of the evaluation, the purified conjugate of the present invention thus obtained had a molecular weight of 1,255 g/mol (FIG. 21), and the highest absorption and the highest emission were shown at 402 nm and 665 nm, respectively (FIG. 22).

2) Increase in Fluorescence Signal Due to a Reducing Agent and Enzyme Action

Meanwhile, in order to analyze the reactivity of the reducing agent/enzyme complex reaction type Ce4-CRRCW conjugate to the reducing agent, the conjugate was treated with reducing agents DTT 2 μM and 5 mM for 6 hours and put into a multifunctional microplate reader to obtain the fluorescence spectrum ($\lambda_{Ex.}$ 400 nm, $\lambda_{Em.}$ 620~850 nm) results. In order to analyze the reactivity to the enzyme, the conjugate was treated with cathepsins B, S, L, and S, or cathepsin B pretreated with cathepsin inhibitor E64 for 6 hours and put into a multifunctional microplate reader to obtain the fluorescence spectrum ($\lambda_{Ex.}$ 400 nm, $\lambda_{Em.}$ 620~850 nm) results. In order to analyze the reducing agent/enzyme complex reaction, 5 mM DTT and cathepsin B enzyme were treated together for 6 hours and put into a multifunctional microplate reader to obtain the fluorescence spectrum ($\lambda_{Ex.}$ 400 nm, $\lambda_{Em.}$ 620~850 nm) results.

Figure 23:
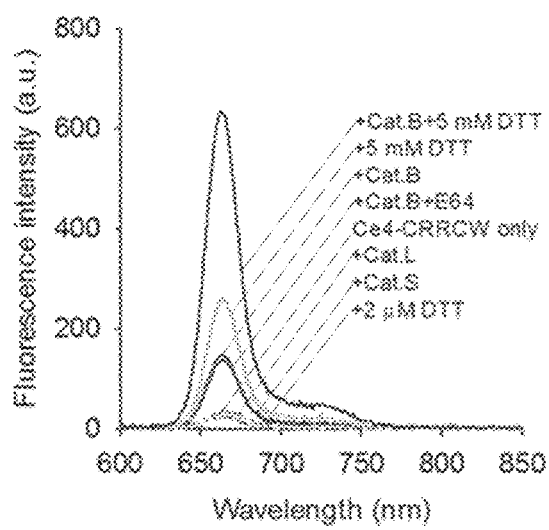
FIG. 23 is fluorescence spectrum data obtained by treating Ce4-CRRCW, which is a photosensitizer-peptide conjugate of Example 5 of the present invention, alone or in combination with DTT as a reducing agent and cathepsin enzymes ($\lambda_{Ex.}$ 400 nm; cathepsin enzyme (cathepsin B, S, L and cathepsin B pretreated with an inhibitor E64) was treated with Ce4-CRRCW for 6 hours, respectively, and DTT as a reducing agent was treated alone with Ce4-CRRCW at concentrations of 2 μM and 5 mM, or DTT 5 mM and cathepsin B were treated together with Ce4-CRRCW and the fluorescence spectrum was analyzed).

According to FIG. 23, it was observed that each of the fluorescence generation was increased when the conjugate was treated with 5 mM DTT or cathepsin B alone. When 5 mM DTT and cathepsin B were simultaneously treated, it was confirmed that the fluorescence intensity was 26 times higher than a control group. When treated with only 5 mM DTT, the fluorescence intensity increased by 10.6 times. When 2 μM DTT, which is the extracellular reducing agent concentration, was treated, the fluorescence intensity did not increase at all. When the conjugate entered the cell, fluorescence and reactive oxygen generation characteristics of the conjugate were activated by the intracellular reducing agent and the enzyme by a single or a combination action.

3) Cell Culturing

SCC7 cancer cell lines were cultured in DMEM (Dulbecco's modified Eagle's medium) medium (Gibco) including 10% FBS and 1% penicillin/streptomycin at 37° C. under 5% carbon dioxide condition.

4) Absorption of the Conjugate in Cancer Cells and Fluorescence Activity Analysis Accordingly SCC7 cancer cells per well were put in a 4-well Lab-Tek chamber per $2 \times 10^5$, and were cultured for 24 hours to allow the cells to be absorbed well. Thereafter, the existing medium was replaced with 500 μl of fresh medium in which the Ce4-RRW conjugate 2 μM was included, and then the cells were cultured for 2 to 6 hours. Finally, the cells were washed three times with the culture medium, and a near-infrared fluorescence image ($\lambda_{Ex.}$ 633 nm, $\lambda_{Em.}$ 646~753 nm) was obtained using a confocal laser microscope.

Experiments were also conducted to analyze whether the conjugate migrates to a lysosome with a high concentration of intracellular reducing agent. In the 8-well Lab-Tek chamber, SCC7 cells were put at a cell number of $5 \times 10^4$ in each well. The cells were cultured for 24 hours to allow the cells to be absorbed well, and then 2 μM the conjugate was added and cultured for 6 hours, followed by washing three times. Thereafter, after replacing the existing medium with fresh medium including 100 nM LysoTracker Blue DND-22 dye, the cells were cultured for 45 minutes. Fluorescent images of the conjugate ($\lambda_{Ex}$ 405 nm, $\lambda_{Em.}$ 625~754 nm) and LysoTracker ($\lambda_{Ex.}$ 405 nm, $\lambda_{Em.}$ 411~497 nm) were obtained for these samples using confocal microscopy.

Figure 24:
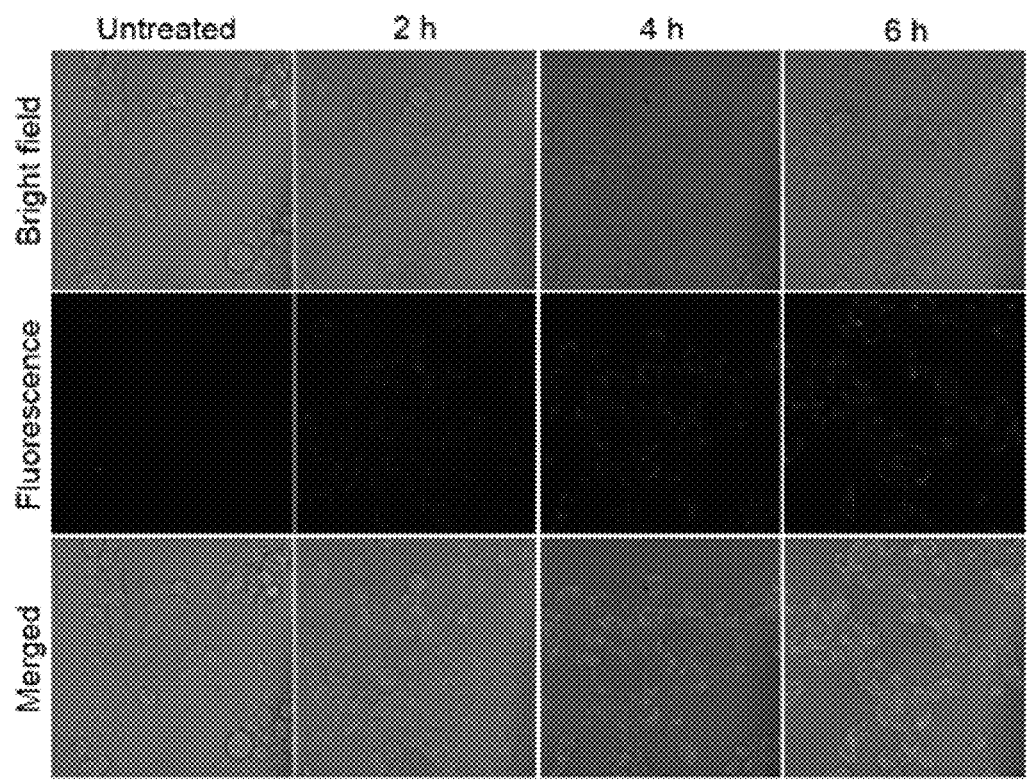
FIG. 24 is a confocal laser microscope photograph obtained by treating Ce4-CRRCW, which is a photosensitizer-peptide conjugate of Example 5 of the present invention with SCC7 cancer cell lines for 2 hours, 4 hours, and 6 hours, respectively.

According to FIG. 24, when the conjugate Ce4-CRRCW was treated on SCC7 cells, it was introduced into cells and showed a strong fluorescence signal. In particular, the intracellular fluorescence intensity was further increased with the lapse of culture time, and fluorescence generation was activated in cancer cells.

Figure 25:
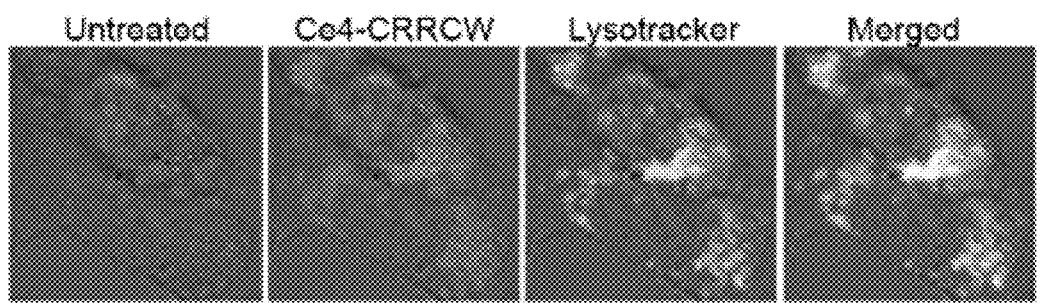
FIG. 25 is a confocal laser microscope photograph obtained by treating SCC7 cells with Ce4-CRRCW, which is a photosensitizer-peptide conjugate of Example 5 of the present invention and further staining lysosomes using LysoTracker.

According to FIG. 25, when a Lysotracker specifically straining a lysosome in a cell was stained together with a conjugate, it was confirmed that there was a site stained jointly. Even when the fluorescence images were superimposed on each other, the position looked superimposed exactly. It was confirmed that the conjugate was located in the intracellular lysosome and activated therein.

As discussed above, the specific portions of the contents of the present invention have been described in detail. Therefore, it is apparent to a person having ordinary skill in the pertinent art that such specific technology is merely a preferable embodiment, and the scope of the present invention is not limited thereto. Accordingly, the substantial scope of the present invention is defined by the appended claims and their equivalents.

The invention claimed is:

1. A photodynamic diagnostic or therapeutic conjugate for treating cancer, wherein the conjugate is represented by the Formula 1:

[Formula 1]

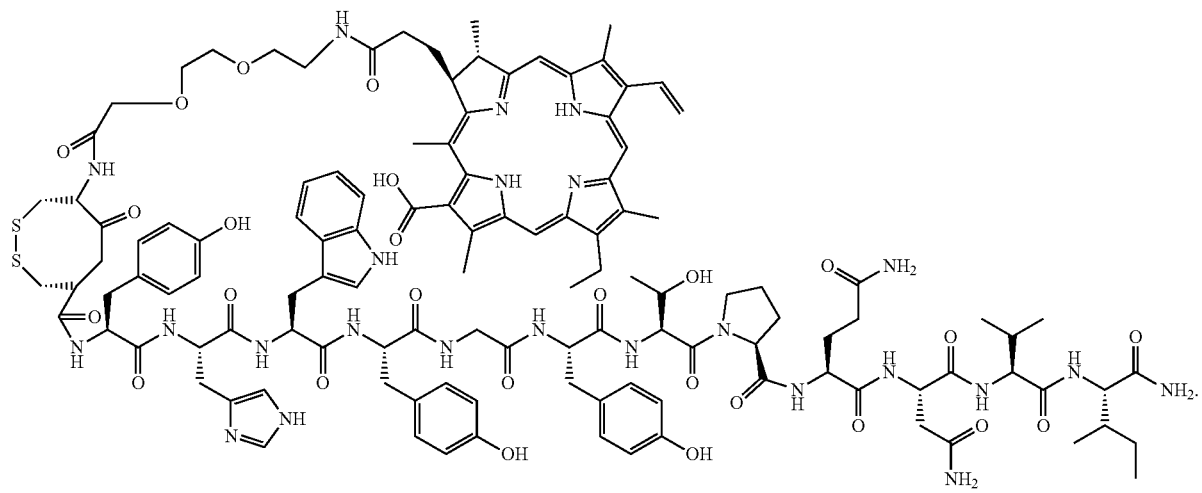

2. A photodynamic diagnostic or therapeutic conjugate for treating cancer, wherein the conjugate is represented by the Formula 2:

[Formula 2]

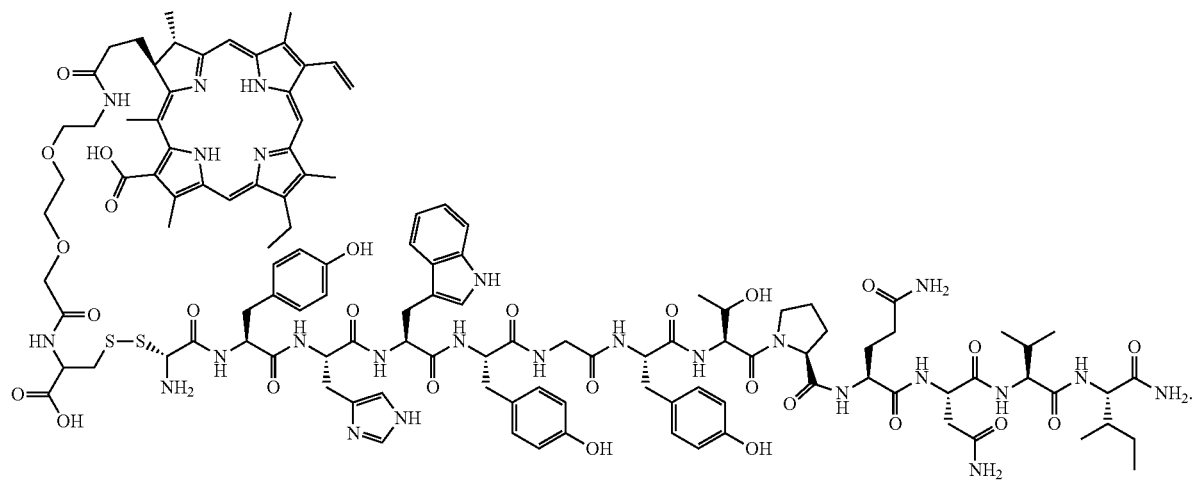

3. A photodynamic diagnostic or therapeutic conjugate for treating cancer, wherein the conjugate is represented by the Formula 3:

[Formula 3]

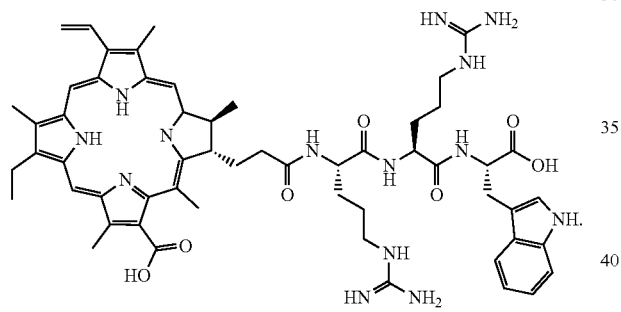

4. A photodynamic diagnostic or therapeutic conjugate for treating cancer, wherein the conjugate is represented by the Formula 4:

[Formula 4]

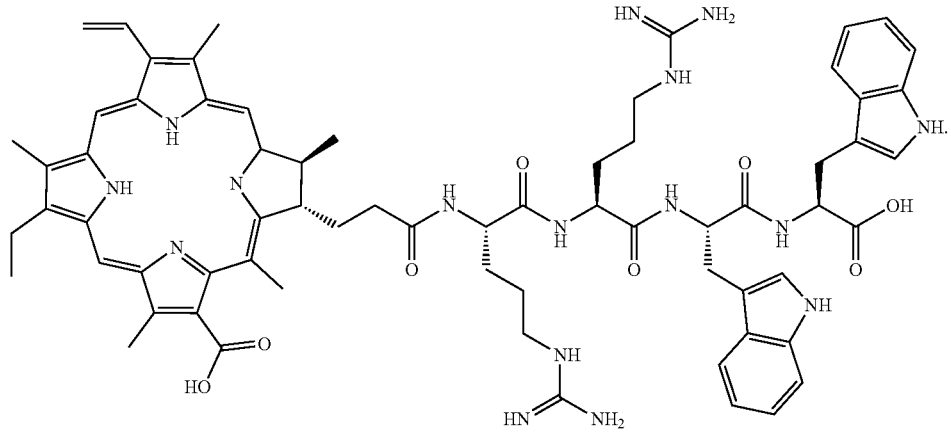

5. A photodynamic diagnostic or therapeutic conjugate for treating cancer, wherein the conjugate is represented by the Formula 5:
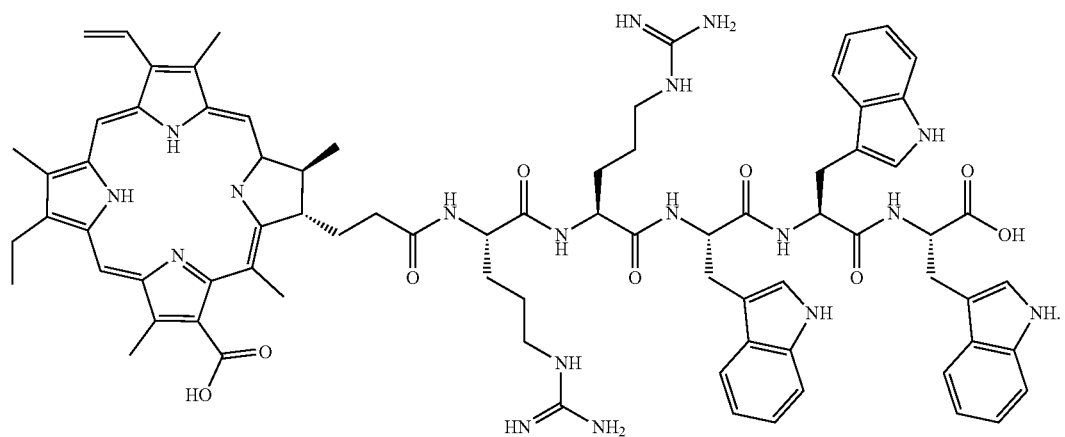
[Formula 5]
6. A photodynamic diagnostic or therapeutic conjugate for treating cancer, wherein the conjugate is represented by the Formula 6:
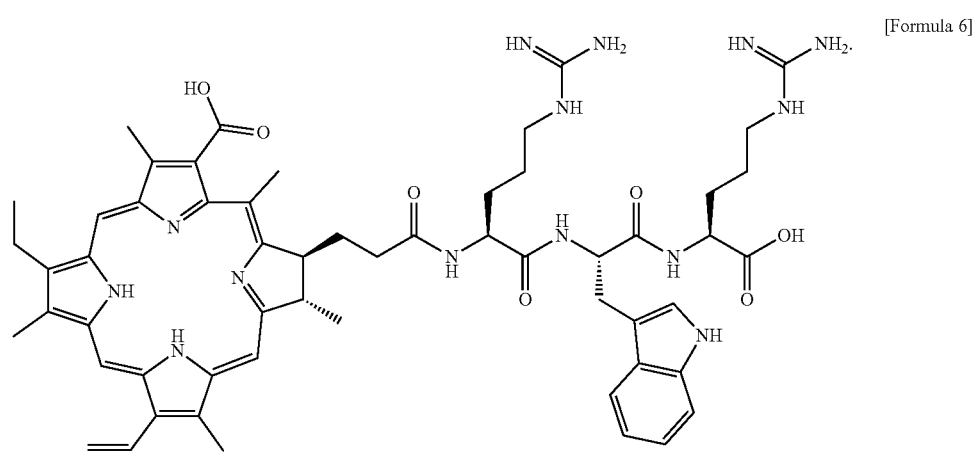 [SMILES: C=Cc1c(C)c2cc3nc(c(C)c4nc(cc5[nH]c(cc1[nH]2)c(C)c5CC)C(C)=C4C(=O)O)[C@@H](CCC(=O)N[C@@H](CCCNC(=N)N)C(=O)N[C@@H](Cc1c[nH]c2ccccc12)C(=O)N[C@@H](CCCNC(=N)N)C(=O)O)[C@@H]3C]
[Formula 6]

7. A photodynamic diagnostic or therapeutic conjugate for treating cancer, wherein the conjugate is represented by the Formula 7:
[Formula 7]
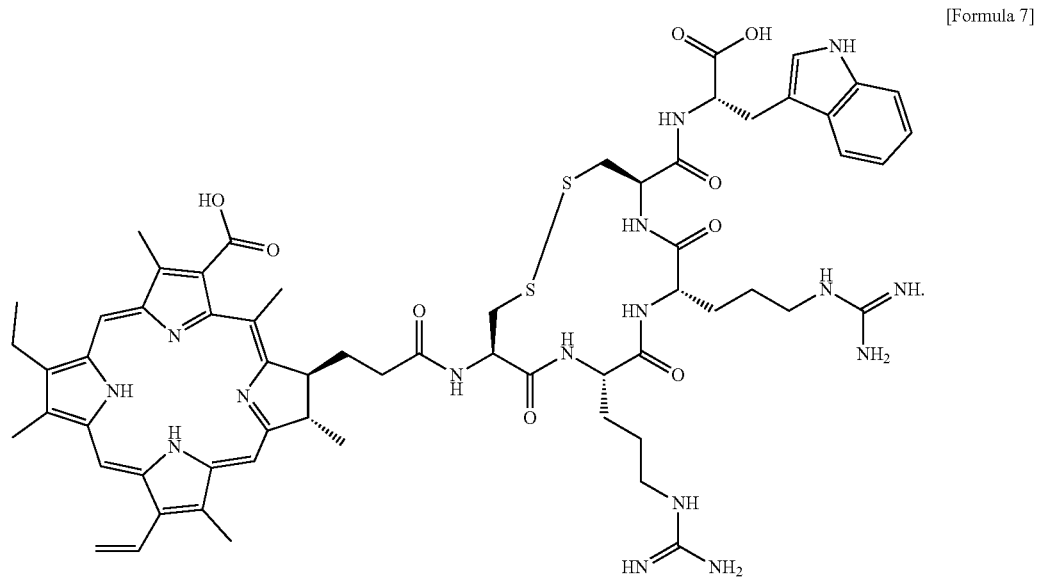 [SMILES: C=Cc1c(C)c2cc3nc(c(C)c4nc(cc5[nH]c(cc1[nH]2)c(C)c5CC)C(C)=C4C(=O)O)[C@@H](CCC(=O)N[C@H]1CSSC[C@@H](C(=O)N[C@@H](Cc2c[nH]c4ccccc24)C(=O)O)NC(=O)[C@H](CCCNC(=N)N)NC(=O)[C@H](CCCNC(=N)N)NC1=O)[C@@H]3C]
* * * * *

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: petide sequence for binding epidermal growth
      factor receptor

<400> SEQUENCE: 1

Tyr His Trp Tyr Gly Tyr Thr Pro Gln Asn Val Ile
1               5                   10
```